United States Patent [19]

Walters et al.

[11] 4,393,327

[45] Jul. 12, 1983

[54] ELECTRIC SPARK TYPE LIGHT SOURCE FOR PRODUCING LIGHT FOR SPECTROSCOPIC ANALYSIS

[75] Inventors: John P. Walters; Steven G. Barnhart, both of Madison, Wis.

[73] Assignee: Wisconsin Alumni Research Foundation, Madison, Wis.

[21] Appl. No.: 287,894

[22] Filed: Jul. 29, 1981

[51] Int. Cl.³ .......................... H05B 7/20; G01J 3/30
[52] U.S. Cl. ............................ 315/241 R; 315/240; 315/243; 315/244; 356/313
[58] Field of Search ................ 315/208, 209 CD, 240, 315/241 R, 242, 243, 244; 356/313, 314

[56] References Cited

U.S. PATENT DOCUMENTS 3,749,975 7/1973 Walters ........................... 315/241 R
3,973,167 8/1976 Walters et al. .................. 315/240 X
4,055,783 10/1977 Walters et al. .................. 315/244 X

OTHER PUBLICATIONS

Walters et al., *Emission Characteristics and Sensitivity in a High-Voltage Spark Discharge*, Analytical Chemistry, Nov. 1965 pp. 1484-1503.

*Primary Examiner*—Eugene La Roche
*Attorney, Agent, or Firm*—Burmeister, York, Palmatier, Hamby & Jones

[57] ABSTRACT

An electric spark type light source for producing light for spectroscopic analysis, comprising an analytical spark gap, an energy storage capacitor, a charging and discharging circuit for alternately charging the capacitor and causing the capacitor to discharge across the spark gap to generate sparks which produce light for spectroscopic analysis, such circuit including at least one inductance coil for causing the discharge current through the spark gap to be oscillatory and pulsating in waveform, the circuit including rectifier means for causing the discharge current through the spark gap to have at least a unidirectional component, and time gate pulse generating means for deriving time gate pulses from the circuit in synchronized relation with the oscillatory pulsating spark gap current for use in selecting repetitive segments of the light from the sparks for spectroscopic analysis. The time gate pulses may be derived from the rectifier current, the capacitor discharge current or the spark gap current. A current transformer, a threshold detector and variable delay means may be employed to generate the time gate pulses. The circuit may comprise a capacitor path including a first inductance coil, a spark gap path across the capacitor path and including a second inductance coil, and a rectifier path in parallel with the spark gap path and including a third inductance coil. The spark gap path may include electronic switching means for initiating the discharge of the capacitor across the spark gap. The rectifier means may take the form of a bridge rectifier having its alternating current input terminals connected to an alternating current power supply for charging the capacitor. The direct current output terminals of the bridge rectifier may be connected into the rectifier path for producing a unidirectional pulsating oscillatory current in the rectifier path, while also causing the oscillatory pulsating spark gap current to have at least a unidirectional component.

33 Claims, 19 Drawing Figures

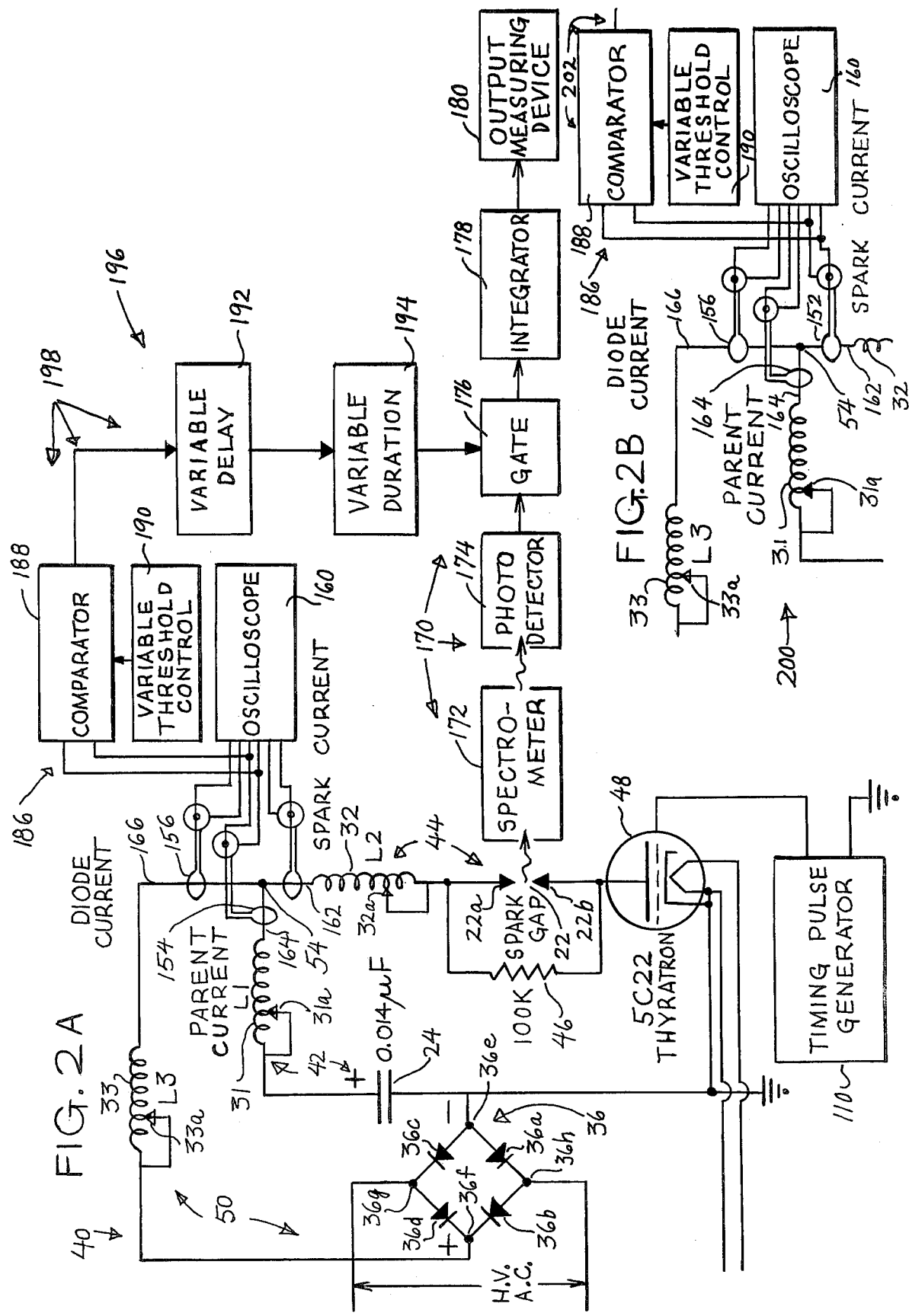

ELECTRIC SPARK TYPE LIGHT SOURCE FOR PRODUCING LIGHT FOR SPECTROSCOPIC ANALYSIS

The U.S. Government has rights in this invention pursuant to Grant No. CHE-79-15195 and IPA No. 0001 awarded by the National Science Foundation.

FIELD OF THE INVENTION

This invention relates to an electric spark type light source for producing light for spectroscopic analysis of metals or other materials which are subjected to electric sparks in the light source. Such light sources are widely used for analyzing metals and other materials in steel mills, foundries and other establishments where such materials are produced or utilized. Moreover, such light sources have found many applications in research laboratories.

BACKGROUND OF THE INVENTION

In certain aspects, the present invention may be regarded as an improvement over the invention disclosed and claimed in the U.S. patent of John P. Walters, No. 3,749,975, issued July 31, 1973 and assigned to the assignee of the present application. Other background patents of general interest are the Walters and Bernier U.S. Pat. No. 3,973,167, issued Aug. 3, 1976; and the Walters and Coleman U.S. Pat. No. 4,055,783, issued Aug. 25, 1977. Another background disclosure is contained in the U.S. patent application of John A. Bernier, entitled High Voltage Spark Source.

OBJECTS OF THE INVENTION

One object of the present invention is to provide a new and improved spark type light source which will provide substantial improvements in the results of spectroscopic analyses.

A further object is to provide a new and improved spark type light source which will reduce the background signal or noise obtained in spectroscopic analysis, in relation to the useful signals produced by spectral lines, so that the signal-to-noise ratio is improved, whereby the spectroscopic analysis may be carried out with a greater degree of sensitivity, precision, repeatability and accuracy.

Another object is to provide a new and improved spark type light source which produces superior results in spectroscopic analysis, yet in many respects is less complex and lower in cost than heretofore.

SUMMARY OF THE INVENTION

To achieve these and other objects, the present invention may provide an electric spark type light source for producing light for spectroscopic analysis, comprising an analytical spark gap, an energy storage capacitor, a charging and discharging circuit for alternately charging the capacitor and causing the capacitor to discharge across the spark gap to produce sparks which generate light for spectroscopic analysis, such circuit including at least one inductance coil for causing the discharge current through the spark gap to be oscillatory and pulsating in waveform, the circuit including rectifier means for causing the discharge current through the spark gap to have at least a unidirectional component, and time gate pulse generating means for deriving time gate pulses from the circuit and synchronized with the oscillatory pulsating waveform of the spark gap current for use in selecting repetitive segments of the light from the sparks for use in spectroscopic analysis. The time gate pulses may be employed to gate the signals from a photodetector in a spectroscopic signal producing and recording system, so that segments of the signal are selected at favorable time intervals to improve the signal to noise ratio, between the useful spectroscopic signals and the background noise, whereby the spectroscopic analyses are carried out with improved sensitivity and accuracy. Generally, the pulses are generated with a timing to select the light produced by off-peak portions of the spark gap current, because such off-peak portions generally produce spectra of reduced complexity with reduced background noise levels, so that the signal to noise ratio is improved.

The time gate pulse generating means may comprise means for deriving a rectifier signal corresponding to the current through such rectifier means, and a threshold detector or other means for converting such rectifier signal into a train of time gate pulses. Pulse processing means may be provided for variably adjusting the timing and duration of the time gate pulses, so that the time gate pulses will correspond with advantageous off-peak portions of the spark current waveform.

In a modified construction, the time gate pulse generating means may include means for deriving a capacitor discharge or parent signal corresponding to the discharge current from the capacitor, and a threshold detector or other means for converting such capacitor discharge signal into a train of time gate pulses. Variable pulse processing means may also be employed to delay or otherwise adjust the time gate pulses, so as to select the light from favorable off-peak portions of the spark current waveform.

In another modification, the time gate pulse generating means may comprise means for deriving a spark current signal corresponding to the discharge current across the spark gap, and a threshold detector or other means for converting the spark gap signal into a train of time gate pulses. Here again, variable means may be employed to process the time gate pulses, so as to select the light from favorable off-peak portions of the spark current waveform.

The time gate pulse generating means may include a current transformer or other means for deriving a wave train signal corresponding to one of the oscillatory pulsating currents in the circuit, due to the discharge of the capacitor across the spark gap, a threshold detector or other means for converting the wavetrain signal into a train of time gate pulses, and in some cases variable delay or other pulse processing means for modifying the train of time gate pulses to select light on a favorable basis from off-peak portions of the spark current waveform.

The charging and discharging circuit preferably includes a capacitor path including a first inductance coil in series with the capacitor, a spark gap path including a second inductance coil in series with the spark gap, and a rectifier path including a third inductance coil in series with the rectifier means. The spark gap path is connected across the capacitor path for receiving the discharge current from the capacitor, and the rectifier path is connected in parallel with the spark gap path. All three coils may be adjustable in inductance. The provision of coils in all three paths makes it possible to minimize the effective damping in the circuit, so that a damped oscillatory waveform of prolonged duration is produced in the capacitor path. The rectifier current has a unidirectional pulsating oscillatory waveform, while the spark current has a pulsating oscillatory waveform having at least a unidirectional component. Preferably, the spark current has a unidirectional pulsating oscillatory waveform. By minimizing the damping in the circuit, the total number of pulses in the damped pulsating waveform of the spark current is increased, so that the time gate pulses are able to select the light from more of the favorable off-peak portions of the spark current waveform.

The rectifier means may be and preferably is in the form of a bridge rectifier having its direct current output terminals connected into the rectifier path. The bridge rectifier has alternating current input terminals which are connected to an alternating current power supply for charging the capacitor. Such power supply may derive its input from the A.C. mains or a computer-controlled power oscillator and may comprise an alternating current power transformer having a high voltage secondary winding connected to the input terminals of the bridge rectifier. The power supply may also include a current limiting impedance for limiting the charging currents supplied by the high voltage secondary winding to the bridge rectifier. Such impedance may be in the form of one or more resistors, connected in series with the high voltage secondary, or active devices functioning as resistance.

With this construction, the bridge rectifier serves the dual purposes of providing the rectifier means in the rectifier path, for causing the spark current to be unidirectional, while also rectifying the alternating current in the charging path for charging the capacitor.

The circuit also preferably comprises a thyratron electronic switching tube, or some other electronic switching means, connected in series with the spark gap path, for initiating or triggering the discharge of the capacitor across the spark gap. The thyratron switching tube has a unidirectional conductivity. The provision of the bridge rectifier or other rectifier means in the rectifier path makes it possible to produce a unidirectional pulsating spark current waveform, so that the thyratron switching tube remains conductive throughout the damped pulsating spark current wavefrom. No additional diode is required across the thyratron tube, because there is no need to carry reverse current. Thus, the bridge rectifier in the rectifier path is the only rectifying device which is required in the circuit.

BRIEF DESCRIPTION OF THE DRAWINGS

Further objects, advantages and features of the present invention will appear from the following description, taken with the accompanying drawings, in which:

FIG. 2A is a schematic circuit diagram, similar to FIG. 1A, but showing a modified construction.

FIG. 2B is a fragmentary schematic circuit diagram, similar to a portion of FIG. 2A, but showing another modified construction.

DETAILED DESCRIPTION OF ILLUSTRATIVE EMBODIMENTS

Figure 1A:
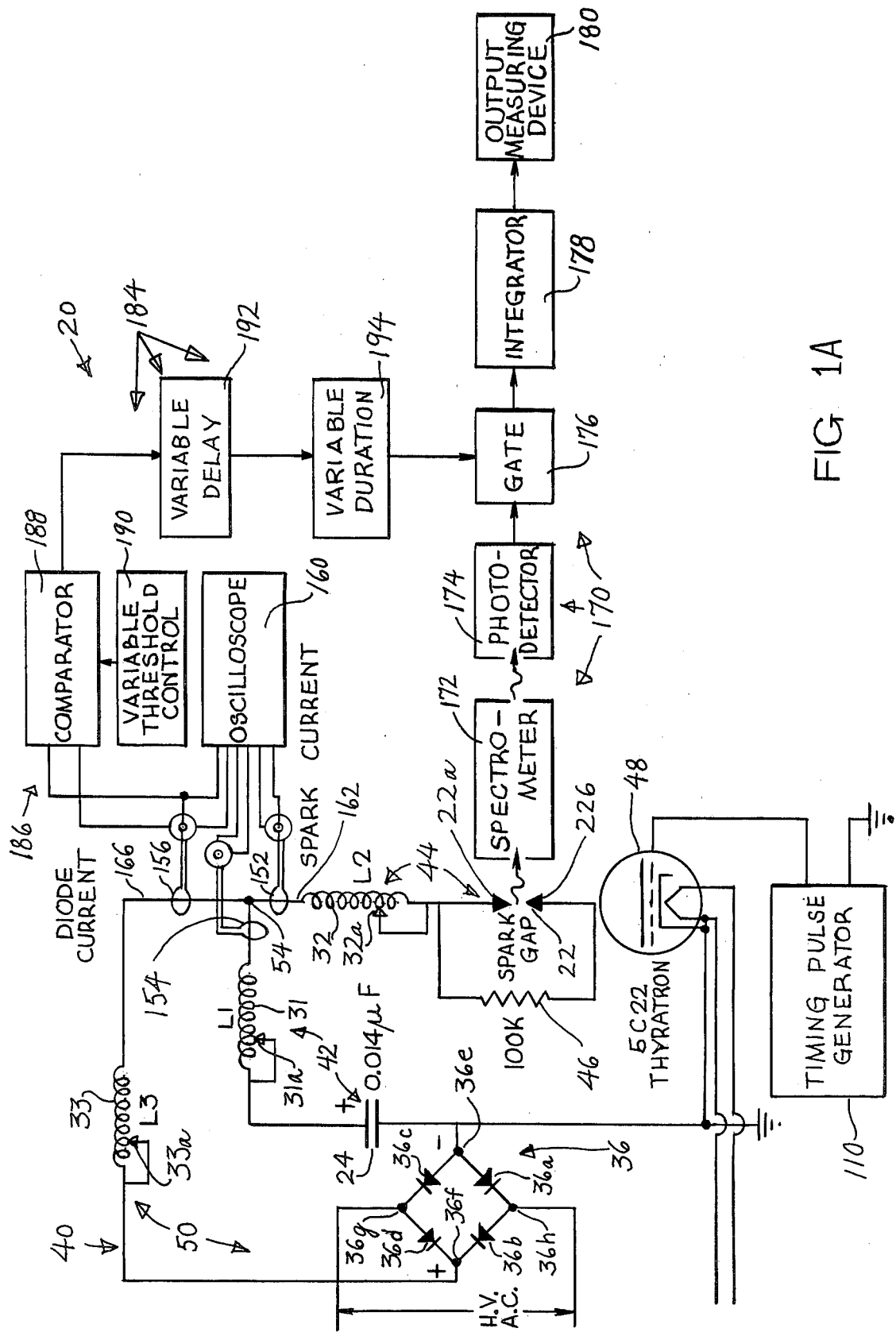
FIGS. 1A and 1B, taken together, constitute a schematic circuit diagram of a spark type light source for producing light for spectroscopic analysis, to be described as an illustrative embodiment of the present invention, a portion of the circuit being shown in both FIGS. 1A and 1B.
Figure 1B:
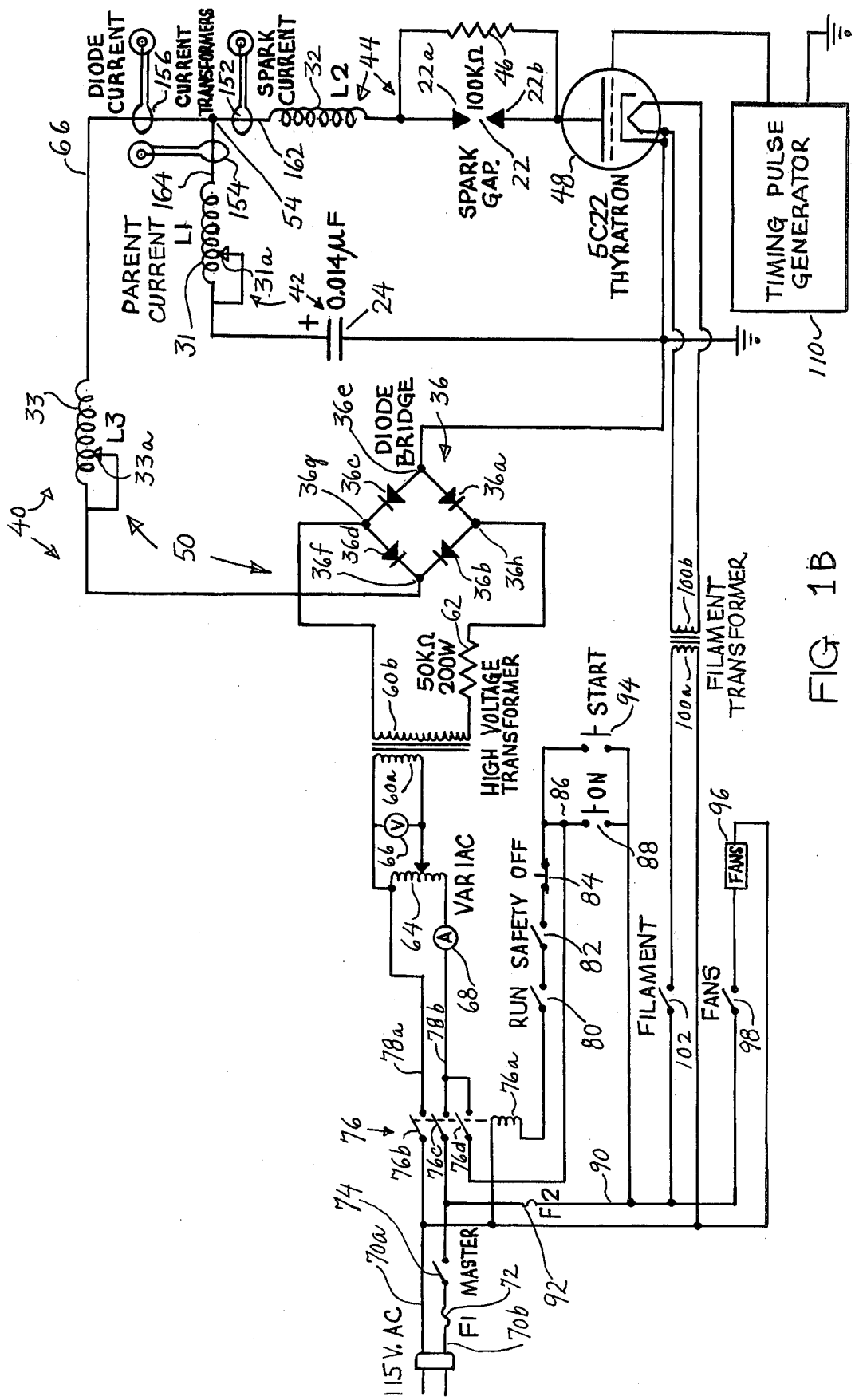

As previously indicated, FIGS. 1A and 1B, taken together, constitute a schematic circuit diagram of an electric spark light source 20, to be described as an illustrative embodiment of the present invention, for producing light for spectroscopic analysis. There is a partial overlapping of FIGS. 1A and 1B, in that some of the components of the light source 20 are shown in both FIGS. 1A and 1B, for clarity of illustration.

The electric spark type light source 20 comprises an analytical spark gap 22, formed between electrodes 22a and 22b, across which electric sparks are produced to generate light for spectroscopic analysis. The material which is to be analyzed is subjected to the electric sparks, so that some of the material is vaporized and electrically excited by the electric sparks. Thus, the material produces light which is analyzed spectroscopically. The material to be analyzed may be placed on one or both of the electrodes 22a and b, or may form the material of one or both of the electrodes. Alternatively, the material to be analyzed may be introduced into the electric spark discharges by a stream of gas or vapor. Alternatively, the material may be a particulate aerosol generated by the sparks, from the electrodes 22a and 22b or from substances placed on them, said aerosol to be transported by the interelectrode gas to another discharge or another device at another location for subsequent analysis.

The light source 20 comprises an energy storage capacitor 24 which is charged to a high voltage and is then discharged across the spark gap 22 to produce an electric spark. In the normal operation of the light source 20, the capacitor 24 is repeatedly charged and discharged to produce a train of electric sparks across the spark gap 22.

The electric spark type light source 20 also comprises at lest one inductance coil which is involved with the capacitor 24 in an oscillating circuit and which causes the capacitor discharge current to be oscillatory, so that the waveform of the capacitor discharge current is in the form of a train of damped oscillations. As will be described in greater detail presently, the light source 20 preferably comprises three adjustable or variable inductance coils 31, 32 and 33, which are also identified as L1, L2 and L3, The coils are provided with means whereby the inductance values of the coil may be changed or varied. As shown, the coils 31, 32 and 33 have adjustable taps 31a, 32a and 33a, whereby the coils may be partially or completely shortcircuited, whereby the inductance of each coil can be varied between a maximum value with the entire coil in the circuit, and a minimum value, representing the inherent inductance of the shortcircuiting conductor, with the entire coil shortcircuited.

The light source 20 also comprises rectifier means 36, whereby the spark gap current is caused to have at least a unidirectional component, so that the spark gap current has a pulsating oscillatory waveform which is at least partially unidirectional. It is preferred that the rectifier means 36 be in the form of a bridge rectifier, comprising four rectifier diodes 36a, 36b, 36c and 36d.

The bridge rectifier 36 does double duty, in that the rectifier is employed not only to cause the spark gap current to be at least partially unidirectional, but also to participate in the charging of the capacitor 24 from a high voltage alternating current source or power supply. Thus, the bridge rectifier 36 has a pair of direct current output terminals 36e and 36f, and a pair of alternating current input terminals 36g and 36h.

The spark type light source 20 includes a charging and discharging circuit 40, whereby the capacitor 24 is repeatedly charged and discharged across the spark gap 22. Such circuit 40 includes all of the components previously mentioned. The circuit 40 includes several interconnected paths, including a capacitor path 42, in which the capacitor 24 and the first inductance coil 31 are connected in series. In this case, one end of the capacitor path 42 is connected to ground, such end being connected to the negative capacitor terminal, which is negatively polarized when the capacitor 24 is initially charged.

The charging and discharging circuit 40 also includes a spark gap path 44, in which the spark gap 22 and the second inductance coil 32 are connected in series. A high value resistor 46 is preferably connected across the spark gap 22 to provide a non-infinite resistance for gap 22 in comparison to thyratron 48 when the latter is in an OFF state. Preferably, the spark gap path 44 also includes switching means for initiating the discharge of the capacitor 24 across the spark gap 22, such switching means preferably being in the form of electronic switching means, such as the illustrated thyratron electronic switching tube 48. In this case, the thyratron 48 is at one end of the spark gap path 44, with the cathode of the thyratron connected to ground.

The charging and discharging circuit 40 comprises a rectifier path 50, in which the rectifier 36 and the third inductance coil 33 are connected in series. The direct current output terminals 36e and 36f of the bridge rectifier 36 are connected into the rectifier path 50. In this case, the negative output terminal 36e is at one end of the rectifier path and is connected to ground. All four of the diodes 36a, 36b, 36c and 36d are connected into the rectifier path 50 and are polarized to be conductive between the terminals 36e and 36f.

Figure 5:
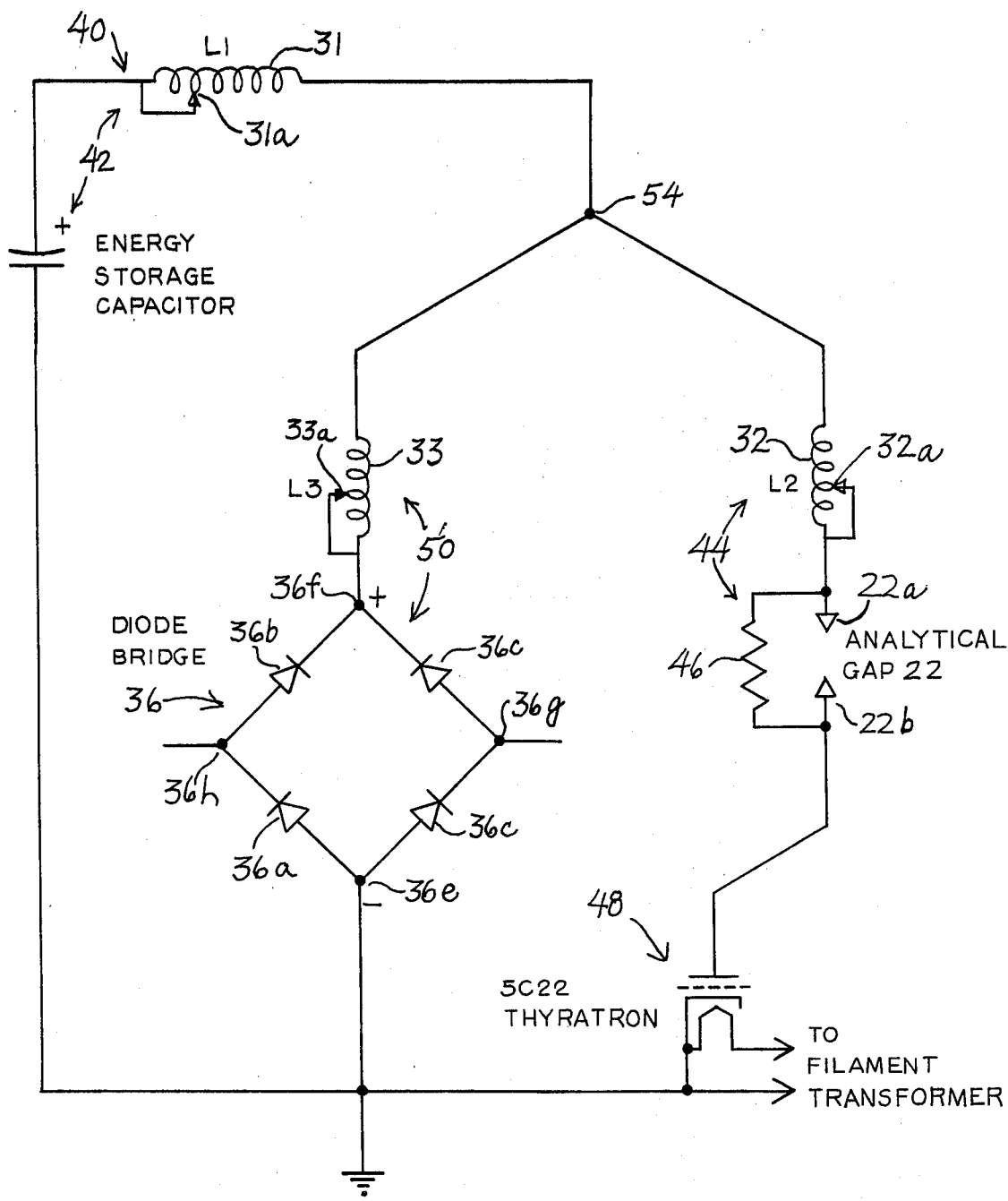
FIG. 5 is a fragmentary circuit diagram, corresponding to a portion of FIG. 1A, but rearranged to show the capacitor path, the spark gap path and the rectifier path more clearly.

The spark gap path 44 is connected across the capacitor pth 42, to receive the discharge current from the capacitor 24. The paths 42 and 44 are connected together at a junction or terminal 54. The rectifier path 50 is connected in parallel with the spark gap path 44. Thus, the rectifier path 50 is also connected to the terminal 54. All three of the paths 42, 44 and 50 are thus connected between the terminal 54 and ground. This arrangement of the paths is particularly clear from FIG. 5, which is a rearrangement of a portion of FIG. 1a.

The charging and discharging circuit 40 also includes a charging path 56 which is connected between the alternating current input terminals 36g and 36h of the diode bridge rectifier 36. The charging path 56 comprises an alternating current power supply 58, including a high voltage a.c. transformer 60 having a primary winding 60a and a high voltage secondary winding 60b. The charging path 56 includes the secondary winding 60b, in series with a current limiting impedance, illustrated as a resistor 62.

To provide for variation of the charging voltage, the primary winding 60a is supplied with alternating current power by a variable autotransformer or variac 64. A voltmeter 66 is connected across the primary winding 60a. An ammeter 68 is connected in series with the input to the variable autotransformer 64.

The variable transformer 64 is supplied with electrical power from a conventional alternating current power source, represented by supply lines 70a and 70b, adapted to deliver alternating current at 115 volts and 60 Hz, or some other suitable voltage and frequency. A fuse 72 and a manual master switch 74 are connected in series with one of the power lines 70a and 70b. In this case, the energization of the variable transformer 64 is controlled by a relay 76 having a coil 76a and three normally open pairs of contacts 76b, 76c and 76d. The contacts 76b and 76c are connected into the leads 78a and b between the respective power lines 70a and 70b and the variable transformer 64.

When the relay coil 76a is energized, the contacts 76b and 76c are closed, and the transformer is thereby connected to the alternating current power lines 70a and 70b.

The energizing circuit for the relay coil 76a starts at the power line 70a and includes the coil 76a in series with a manually operable RUN switch 80, a manually operable SAFETY switch 82, a normally closed push button OFF switch 84, and the relay contacts 76d, which serve as holding contacts. The relay contacts 76d are connected between the power lead 78b and a junction lead or terminal 86, connected to the OFF switch 84. A normally open push button ON switch 88 is connected between the junction 86 and a power lead 90, connected through a fuse 92 to the power line 70b. A normally open push button START switch 94 is connected in parallel with the ON switch 88.

The power supply 58 includes cooling fans 96, connected in series with a switch 98 between the power line 70a and the power lead 90. The power supply 58 also includes a filament transformer 100 having primary and secondary windings 100a and 100b. The secondary winding is connected to the filament or heater of the thyratron switching tube 48. The primary winding 100a is connected in series with a filament supply switch 102 between the power line 70a and the power lead 90.

When the switch 74 and the relay contacts 76b and 76c are closed, the primary winding 60a of the alternating current power transformer 60 is supplied with alternating current power. An alternating current voltage is developed by the secondary winding 60b and is rectified by the diode bridge rectifier 36 to produce a full wave rectified voltage which charges the capacitor 24 through the inductance coils 31 and 33. The capacitor 24 remains charged as long as the thyratron switching tube 48 is nonconductive. When the thyratron tube 48 is triggered into conductivity, the capacitor 24 is connected across the spark gap 22 through the inductance coils 31 and 32. The capacitor voltage is sufficient to break down the spark gap 22, so that an electric spark is produced across the spark gap. Thus, the capacitor 24 is discharged across the spark gap 22.

The thyratron electronic switching tube 48 is triggered into conductivity by pulses applied between the grid and the cathode of the tube 48. Such triggering pulses may be supplied by a timing pulse generator 110, which may supply triggering pulses at regular or irregular intervals, as desired, or as determined by various parameters.

In some cases, the timing of the thyratron triggering pulses is related to the timing of the 60 Hz power. Thus, a particular number of timing pulses may be produced during each cycle or half-cycle of the 60 Hz power. However, in other cases, the timing of the pulses may be unrelated to the 60 Hz power.

In some cases, the timing of the thyratron triggering pulses may be related to the capacitor charging voltage. For example, the triggering pulses may be timed so that each pulse occurs at the same level of capacitor charging voltage. In some cases, the timing of the thyratron triggering pulses is related to both the capacitor charging voltage and the timing of the 60 Hz power.

If desired, the timing pulse generator 110 may be constructed and operated in the manner disclosed and claimed in the Walters and Coleman U.S. Pat. No. 4,055,783, issued Oct. 25, 1977, and entitled SPARK SOURCE WITH REGULATION OF SPARK MAGNITUDE BY CONTROL OF SPARK TIMING.

When the high voltage alternating current power supply 56 is energized, the energy storage capacitor 24 is charged by the high alternating voltage which is developed by the secondary winding 60b of the high voltage transformer 60 and is rectified by the diode bridge rectifier 36. The charging voltage is applied to the capacitor 24 through the inductance coils 33 and 31, which, however, do not have any significant effect upon the charging current, because the coils do not have a significant impedance at 60 Hz. The charging current is limited by the resistor 62.

As long as the thyratron switching tube 48 is nonconductive, the capacitor 24 remains charged. When the tube 48 is rendered conductive by a triggering pulse applied to its grid by the timing pulse generator 110, the full capacitor voltage is applied across the spark gap 22. During normal operation, the capacitor charging voltage and the spark gap 22 are adjusted so that the capacitor voltage breaks down the gap and produces a spark across the gap 22, whereby the capacitor 24 is discharged across the gap 22.

Figure 3A:
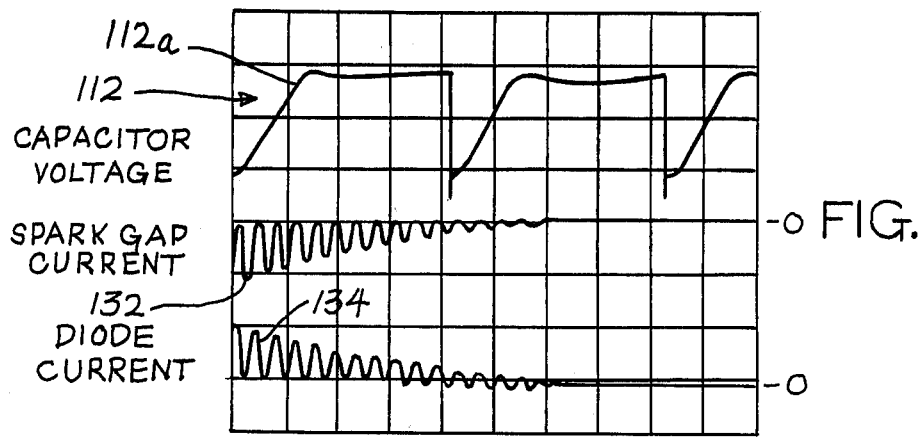
FIG. 3A is a reproduction of oscillograms representing a capacitor voltage during the charging and discharging cycle, the spark gap current and the diode current in the spark type light source.

A sample waveform of the capacitor voltage during the charging and discharging cycles is represented by the upper trace 112 in FIG. 3A. The rising portion 112a of the trace 112 represents the charging of the capacitor 24. The abrupt dropping portion 112b of the trace 112 represents the breakdown of the spark gap 22 and the discharge of the capacitor 24 due to the spark discharge across the spark gap 22. The oscillogram 112 of FIG. 3A represents the situation where the pulses from the timing pulse generator 110 are timed so that there is a single spark discharge during each half cycle of the 60 Hz alternating current power supply.

The other oscillogram traces in FIGS. 3A, 3B, 4A and 4B represent the waveforms of the spark gap current and the diode or rectifier current during the discharge of the capacitor 24, as will be described in greater detail presently. It will be noted that these currents are pulsating, oscillatory and unidirectional, under the conditions represented by these oscillograms. However, the waveforms of the spark gap current and the diode current can be adjusted by adjusting the three inductance coils 31, 32 and 33.

Figure 6:
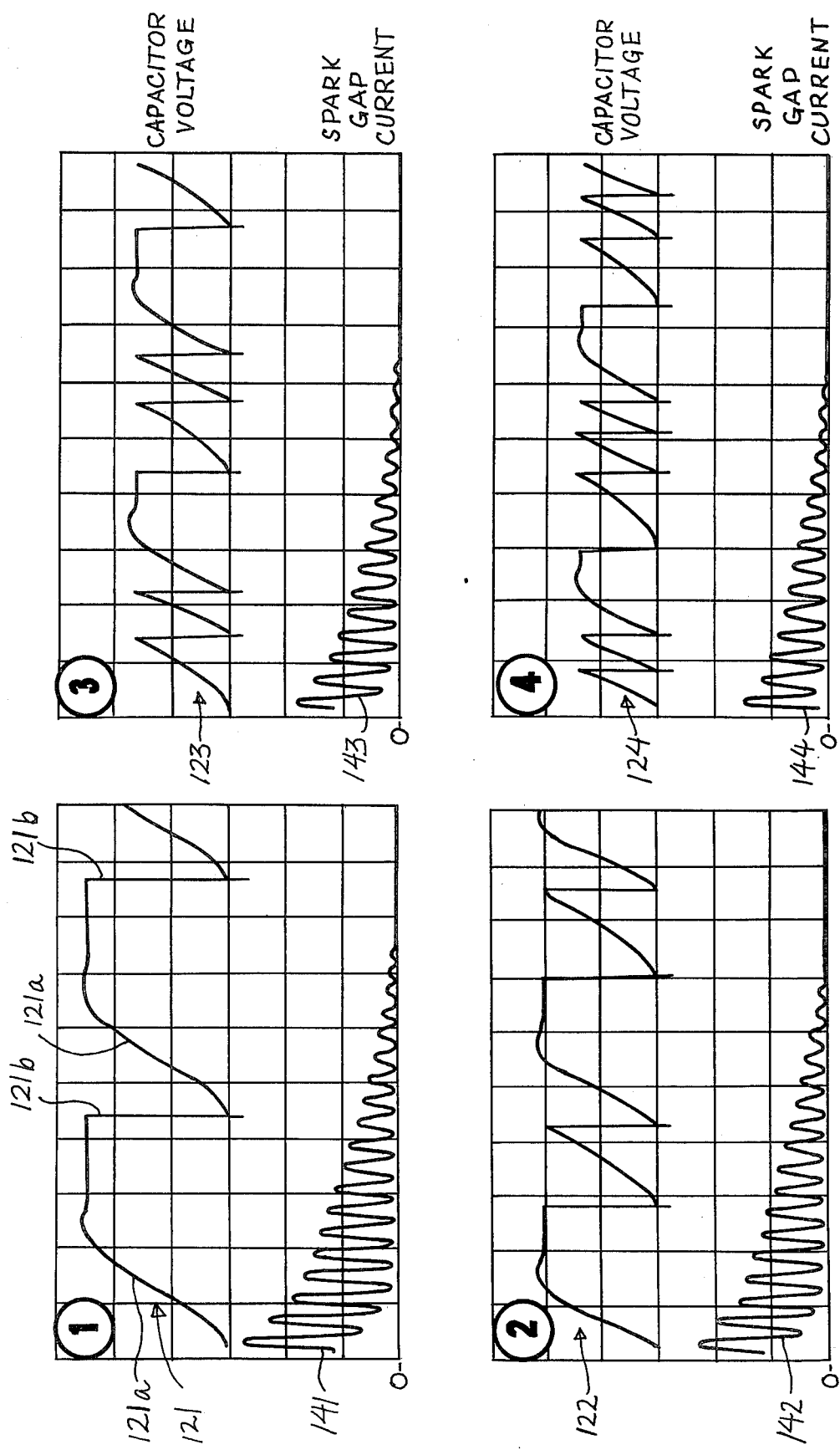
FIG. 6 comprises reproductions of four different sets of oscillograms, marked 1, 2, 3 and 4, representing the capacitor voltage and spark gap current waveform, for different operating conditions, in which there are one, two, three and four spark discharges for each half cycle of the 60 Hz A.C. power supply, the time base for the capacitor voltage being 2 milliseconds per division, while the time base for the spark gap current is 20 microseconds per division.

FIG. 6 shows four additional sample oscillograms 121, 122, 123 and 124, representing the capacitor voltage as the capacitor 24 is repeatedly charged and discharged. The capacitor voltage oscillogram 121 is similar to the oscillogram 112 of FIG. 3A, representing an adjustment of the timing pulse generator 110 so as to produce a single spark discharge during each half cycle of the 60 Hz alternating current power supply. Each cycle of the capacitor voltage oscillogram 121 has a rising portion 121a, representing the charging of the capacitor 24, and an abruptly falling portion 121b, representing the production of the spark and the discharge of the capacitor across the spark gap 22.

The second capacitor voltage oscillogram 122 of FIG. 6 represents a different adjustment of the timing pulse generator 110, whereby two sparks are produced during each half cycle of the 60 Hz alternating current. The capacitor voltage oscillograms 123 and 124 represent still different adjustments, whereby three and four sparks, respectively, are produced during each half cycle of the 60 Hz alternating current. It will be seen that each of the oscillograms 122, 123 and 124 has alternate rising portions, representing the charging of the capacitor, and abruptly falling portions, representing the discharge of the capacitor across the spark gap 22. The lower traces in the four sets of oscillograms of FIG. 6 represent the waveform of the spark gap current, which is pulsating, oscillatory and unidirectional, for the conditions of adjustment represented by the oscillograms.

Figure 11:
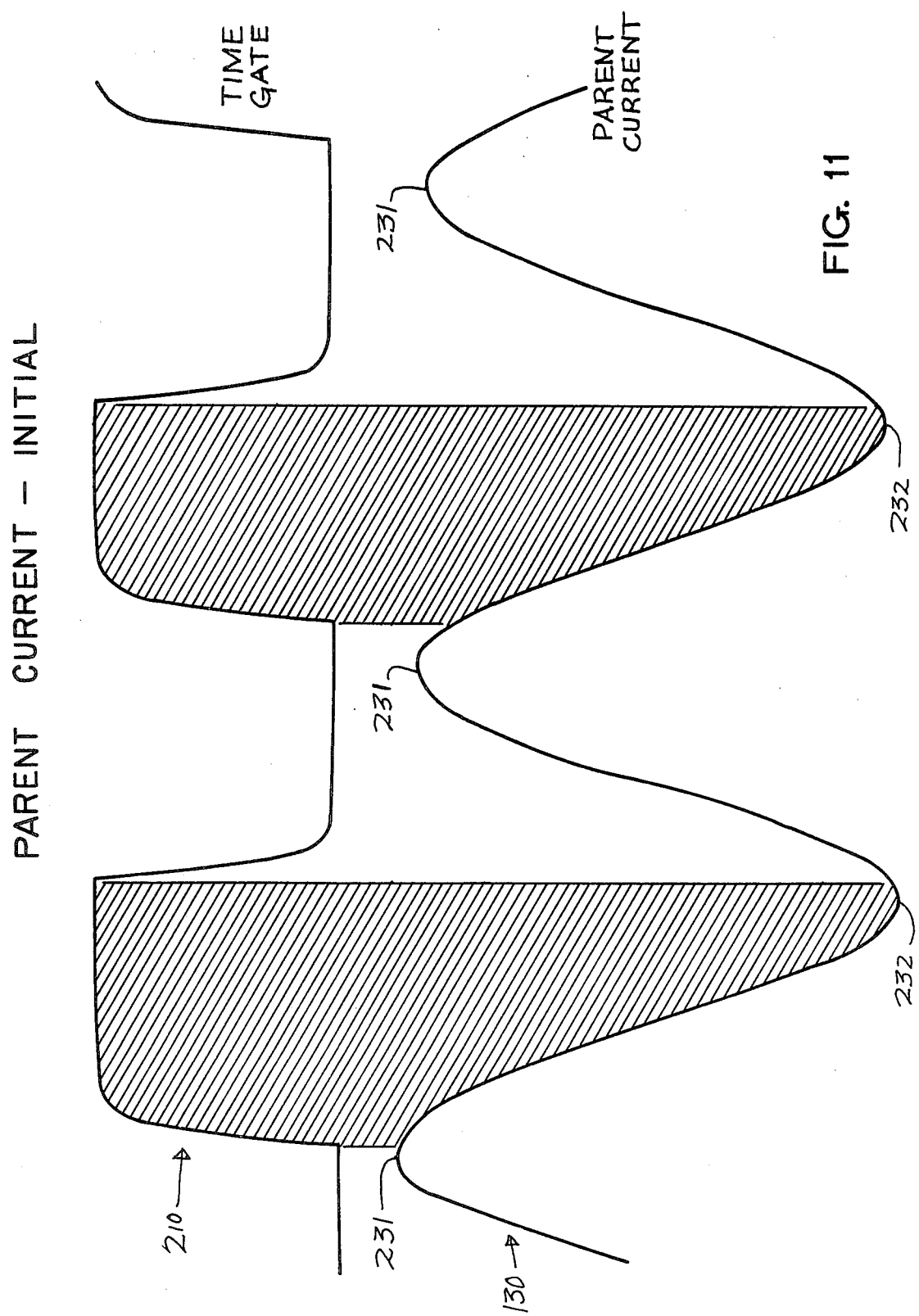
FIG. 11 comprises fragmentary greatly enlarged waveform diagrams, corresponding to the initial portion of FIG. 9, showing the relationship between the parent or capacitor current waveform and the time gate pulses.
Figure 12:
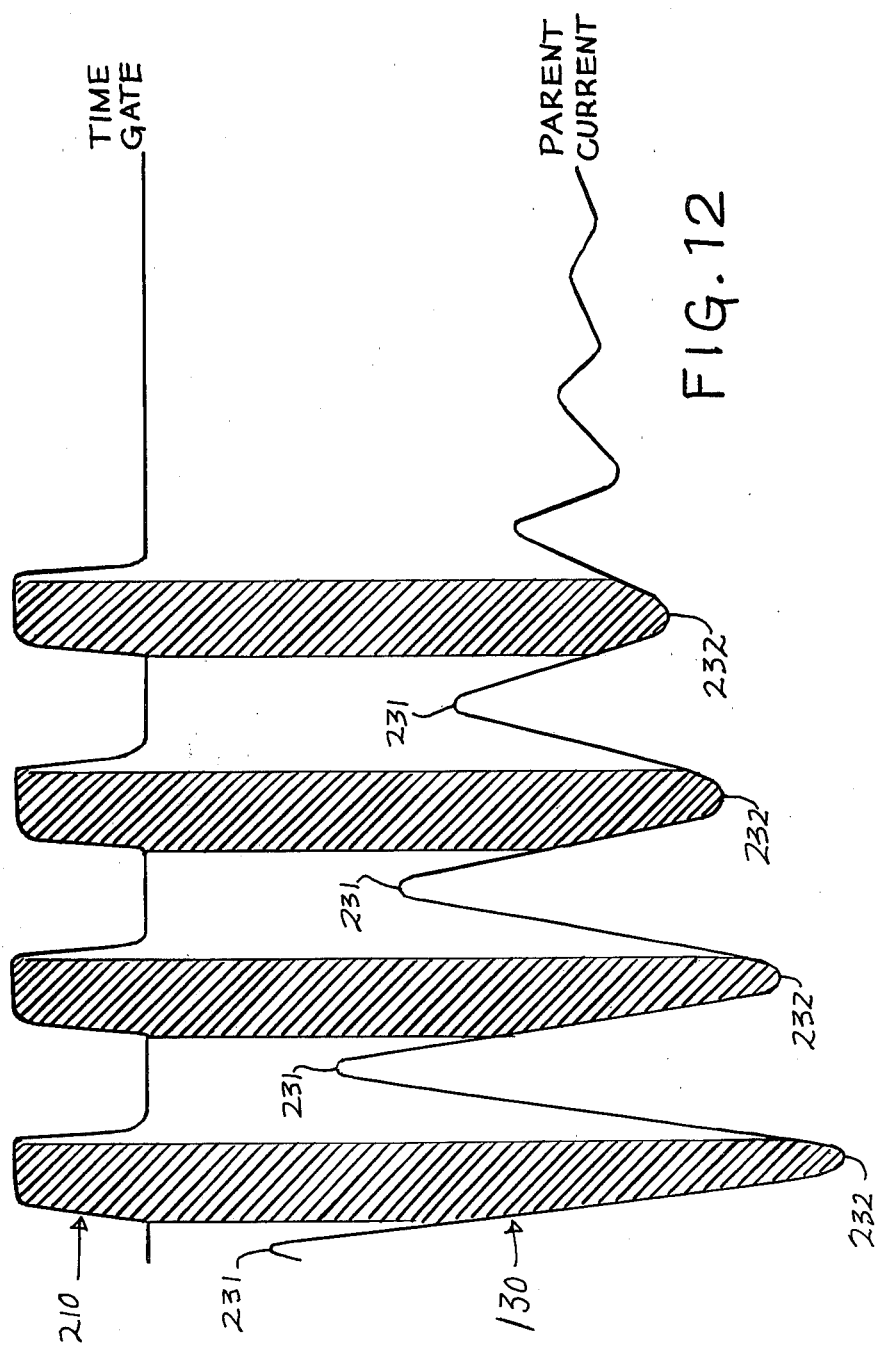
FIG. 12 comprises greatly enlarged waveform diagrams, corresponding to the final portion of FIG. 9, showing the relationship between the parent or capacitor current waveform and the time gate pulses.

The discharging circuit for the capacitor 24 contains not only the capacitor and the spark gap 22, but also the three inductance coils 31, 32 and 33. Due to the presence of both capacitance and inductance, the capacitor discharge current is in the form of a damped oscillatory wave train, as represented by several sample waveforms in the drawings, including the upper waveform 126 in FIG. 7A, the upper waveform 128 in FIG. 7B, and the upper oscillogram 130 in FIG. 8. These waveforms represent the capacitor or parent discharge current during the discharge of the capacitor in the spark discharge across the spark gap 22. An enlarged version of the damped oscillatory wave train 130 is shown in FIG. 9, and even greater enlargements are shown in FIGS. 11 and 12.

Due to the presence of the rectifier or diode means 36 in the circuit 40, the spark current, due to the discharge of the capacitor 24 across the spark gap 22, has a pulsating oscillatory waveform with at least a unidirectional component, and preferably is unidirectional. The diode current in the diode or rectifier path 50 has a unidirectional pulsating oscillatory waveform. The waveforms of the spark current and the diode current are adjustable by adjusting the three inductance coils 31, 32 and 33.

The waveforms of the spark gap current and the diode or rectifier current are shown by sample oscillograms 132 and 134 in FIG. 3A. The vertical scale for these oscillograms 132 and 134 is 100 amperes per division. The horizontal scale is 20 microseconds per division. As to the capacitor voltage oscillogram 112 of FIG. 3A, the vertical scale is 5000 volts per division. The horizontal scale is 2 milliseconds per division.

The spark current oscillogram 132 and the diode current oscillogram 134 of FIG. 3A were produced with the following inductance values: coil 31, 84.9 microhenrys; coil 32, 28.8 microhenrys; coil 33, 44.4 microhenrys. The charging voltage was approximately 10 kiloVolts.

Figure 3B:
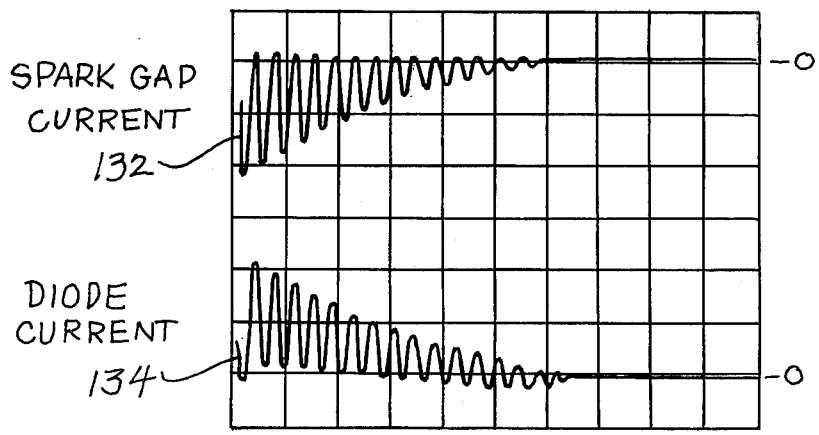
FIG. 3B is a reproduction of oscillograms representing the spark gap current and the diode current for a charging voltage of 10000 volts.

FIG. 3B shows enlarged or expanded versions of the spark current waveform 132 and the diode current waveform 134. The vertical scale in FIG. 3B is 50 amp/division, while the horizontal scale is the same as before, 20 microseconds/division.

Figure 4A:
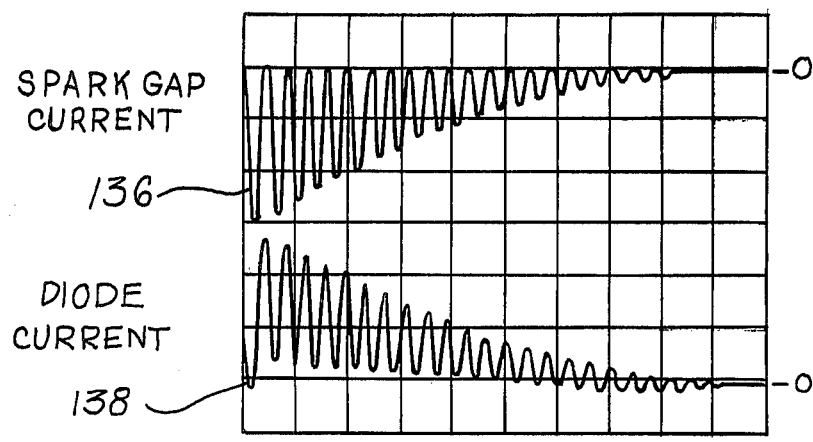
FIG. 4A is a reproduction of additional oscillograms representing the spark gap current and the diode current for a charging voltage of 13,000 volts.
Figure 4B:
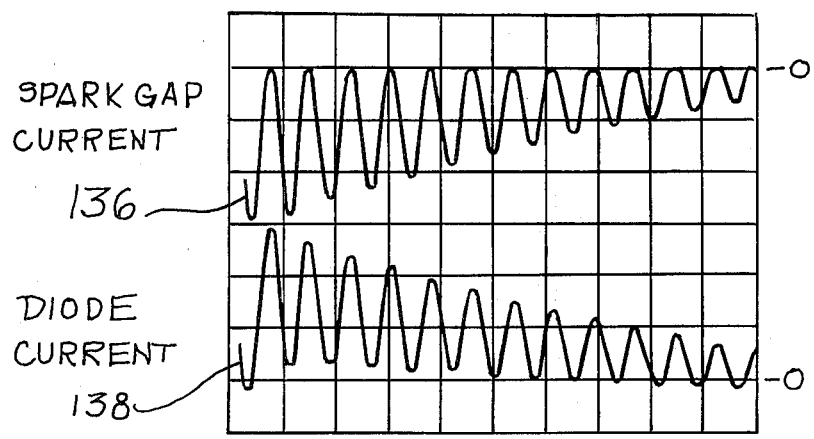
FIG. 4B is a reproduction of oscillograms similar to those of FIG. 4A, but with a time base of 10 rather than 20 microseconds per division.

FIGS. 4A and 4B show spark gap current and diode current oscillograms 136 and 138, respectively, for an increased capacitor charging voltage of 13 kiloVolts. For FIG. 4A, the vertical scale is 50 amp/div., while the horizontal scale is 20 microsec/div. In FIG. 4B, the vertical scale remains at 50 amp/div., but the horizontal scale is 10 microseconds per division, with the result that the oscillograms 136 and 138 are expanded along the horizontal axis.

FIG. 6 comprises four different spark current waveforms 141, 142, 143 and 144, corresponding with the four different capacitor voltage oscillograms 121-124. As in the other examples, the spark current has a waveform which is unidirectional, pulsating and oscillatory. In these four sets of oscillograms, the capacitor voltage oscillograms 121-124 have a voltage scale of 5 kiloVolts/division, and a time scale of 2 milliseconds/division. The spark current oscillograms 141-144 have a current scale of 50 amp/div. and a time scale of 20 microseconds/division.

Figure 7A:
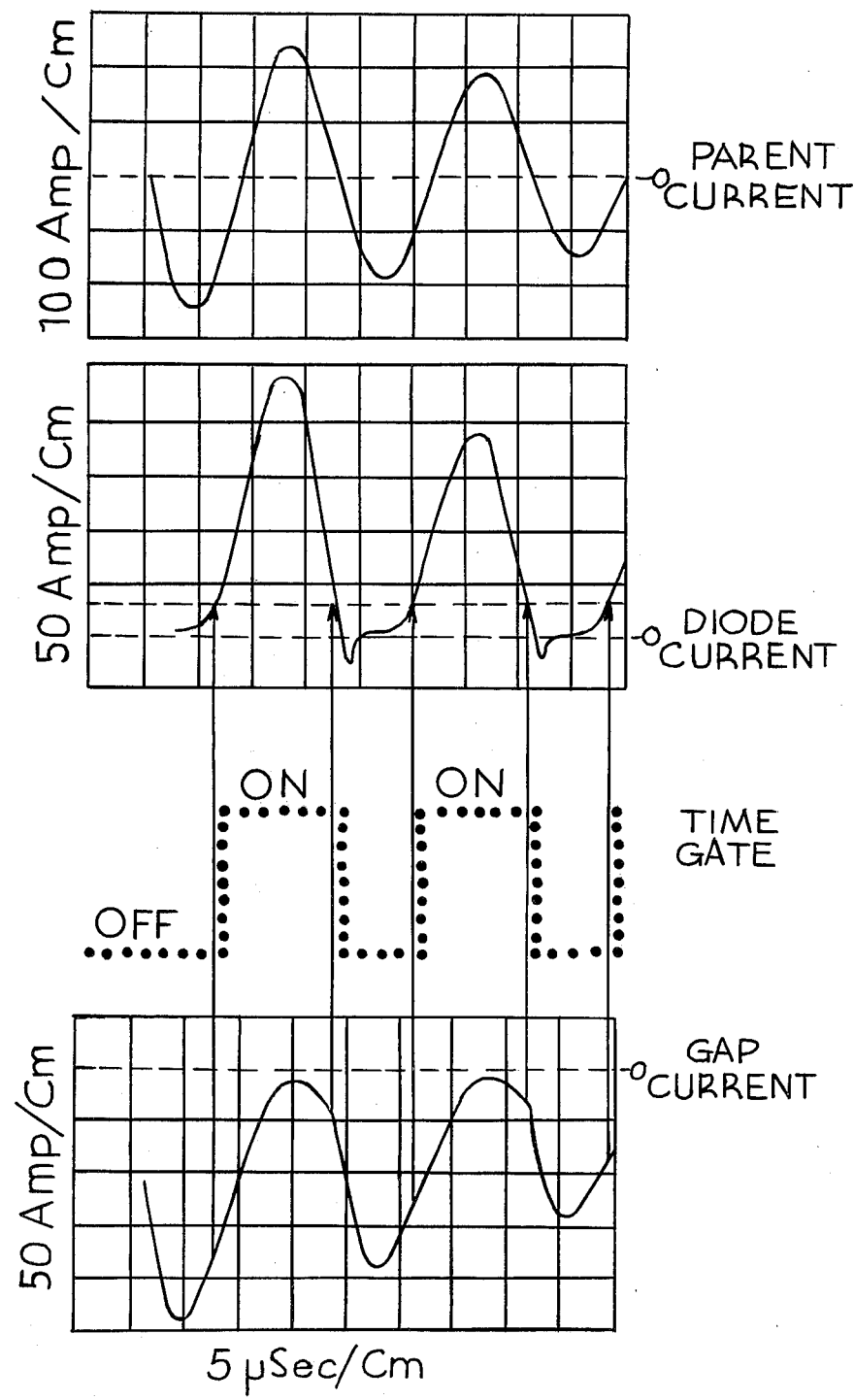
FIG. 7A comprises sample waveform diagrams representing the parent or capacitor current, the diode current, the spark gap current and the time gate pulses, which in this case are derived from the diode current by a threshold detector.

The waveform diagrams of FIG. 7A include a spark gap current waveform 146 and a diode current waveform 148, corresponding with the capacitor or parent current waveform 126. The current and time scales are indicated in FIG. 7A. Here again, the spark and diode current waveforms 146 and 148 are pulsating, oscillatory and unidirectional.

Figure 7B:
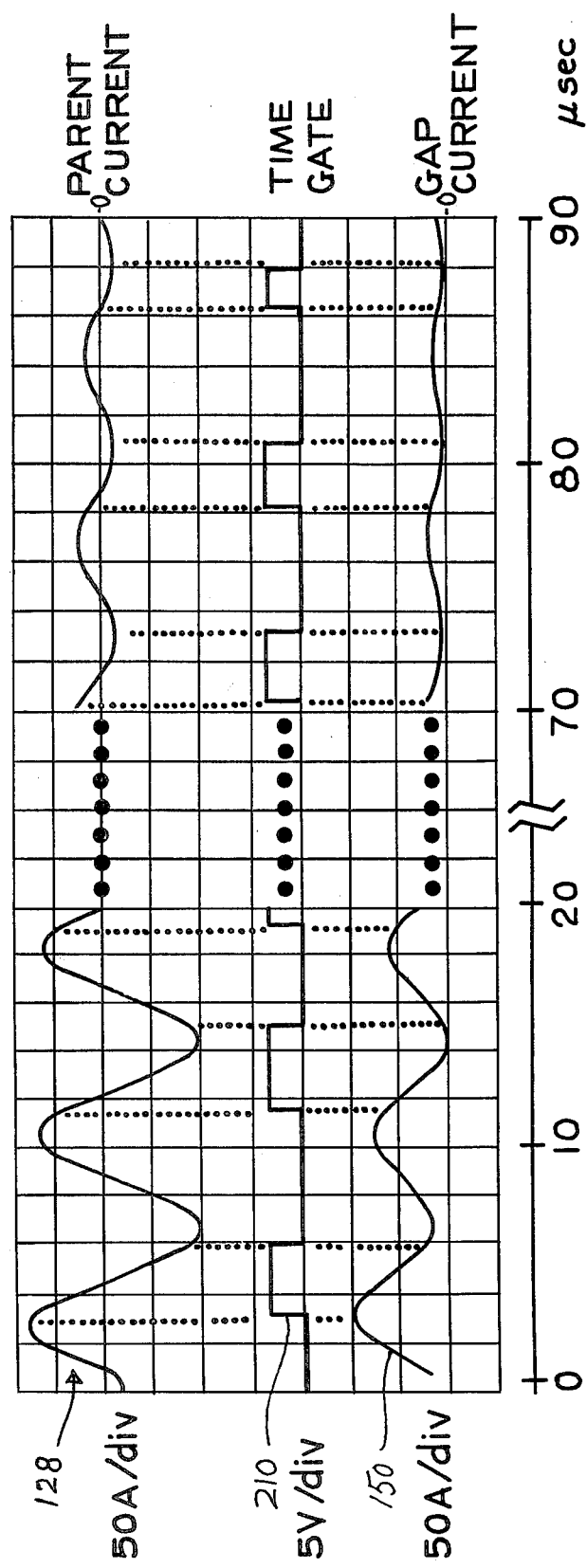
FIG. 7B comprises additional sample waveform diagrams, somewhat similar to FIG. 7A, but with an extended time base, showing sample relationships involving the parent or capacitor current, the spark gap current, and the time gate pulses.

FIG. 7B includes another sample spark gap current waveform 150, corresponding with the parent or capacitor current waveform 128. The waveform diagrams of FIG. 7B are expanded along the time axis, in that the scale is approximately 2 microseconds per division.

Figure 8:
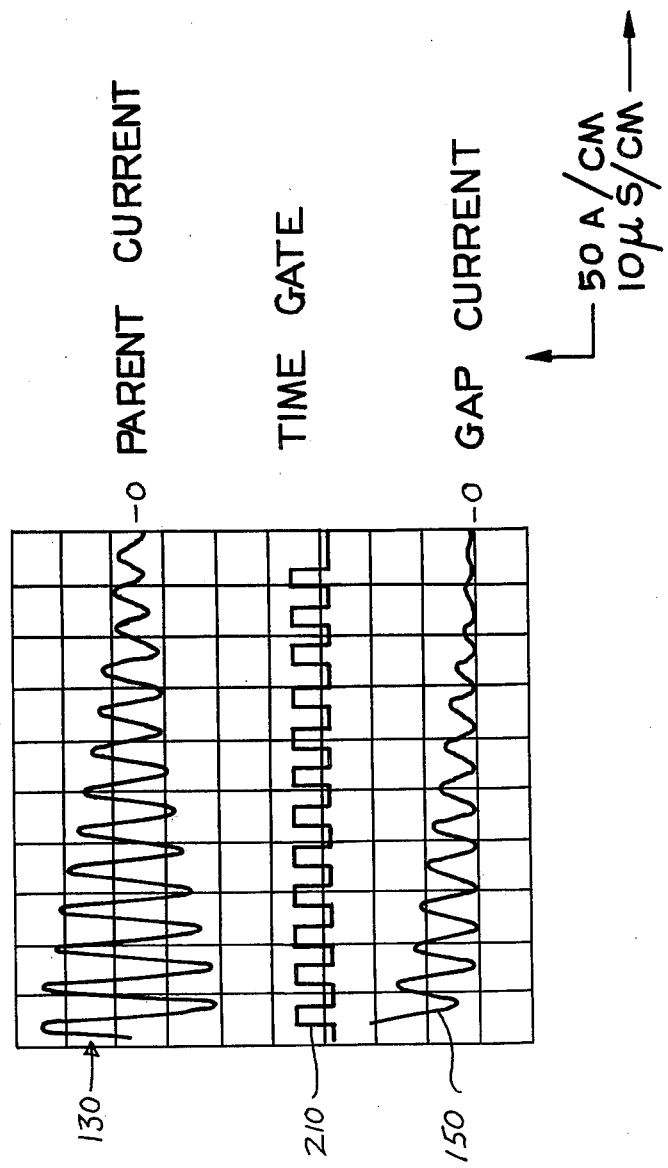
FIG. 8 is a reproduction of additional sample oscillograms representing the parent or capacitor current, the spark gap current, and the time gate pulses.
Figure 9:
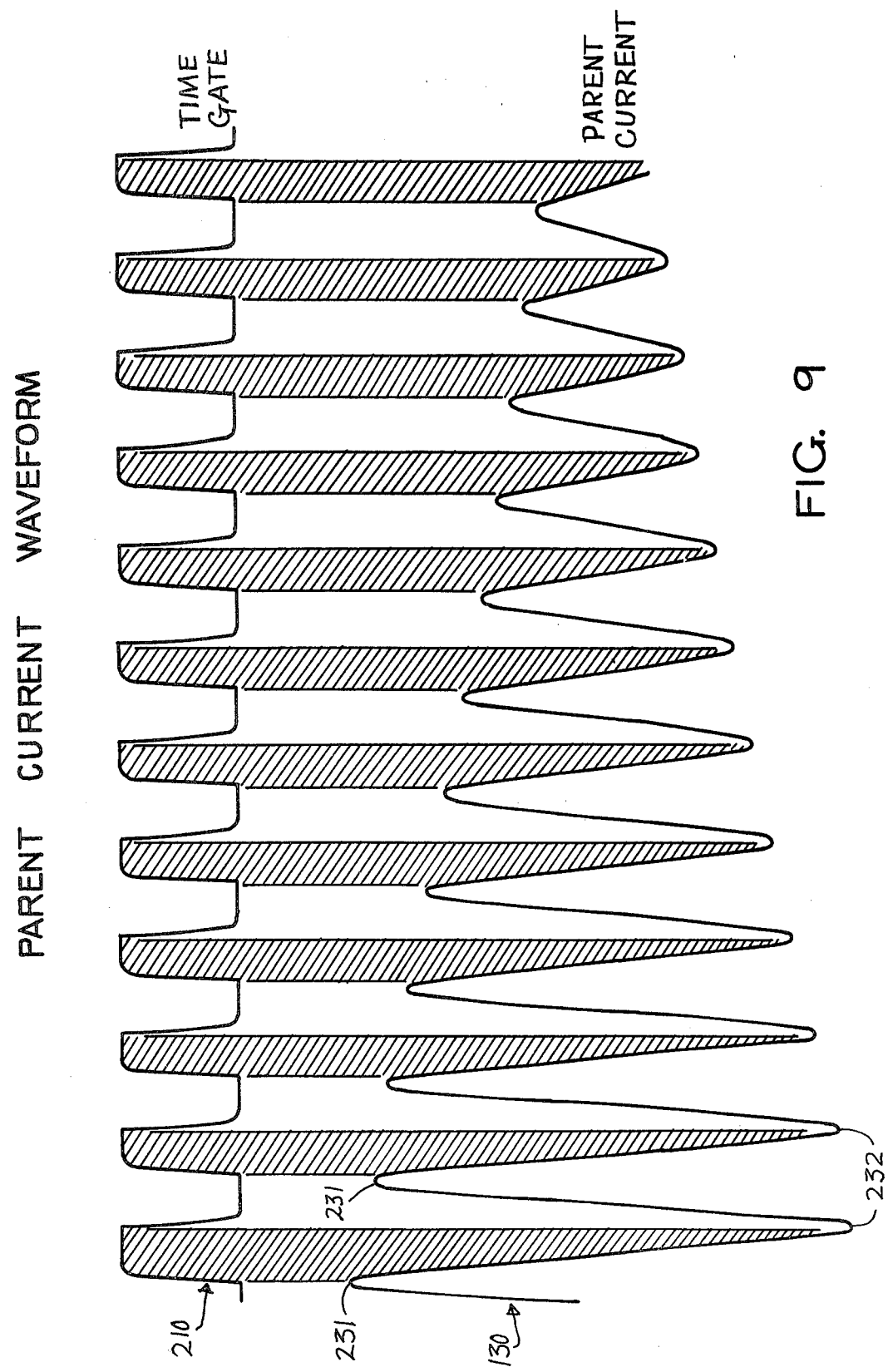
FIG. 9 comprises waveform diagrams, similar to a portion of FIG. 8, but with enlarged scales along both axes, showing the relationship between the time gate pulses and the parent or capacitor current waveform.
Figure 10:
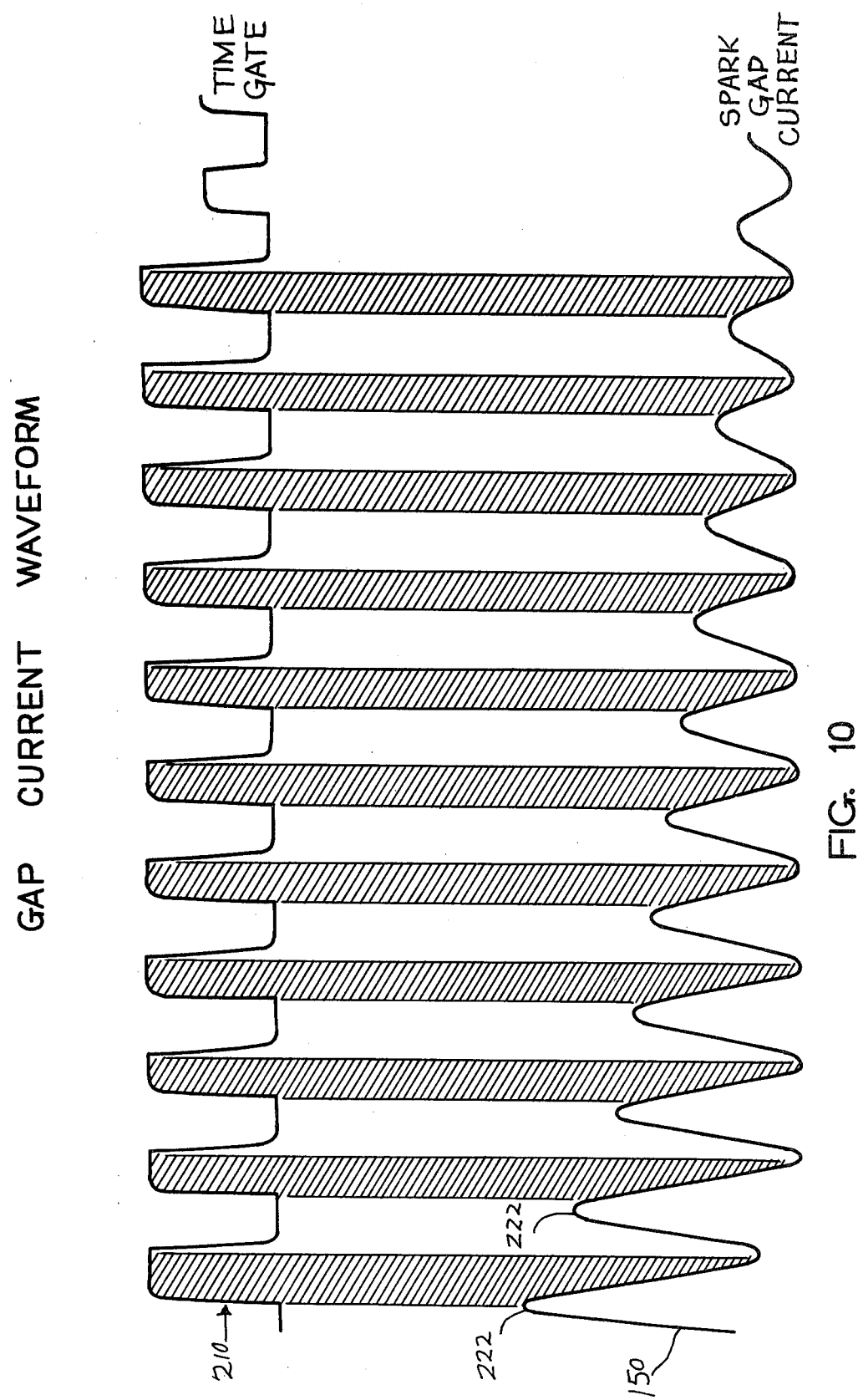
FIG. 10 comprises waveform diagrams, similar to a portion of FIG. 8, but with expanded scales along both axes, showing the relationship between the time gate pulses and the spark gap current waveform.
Figure 13:
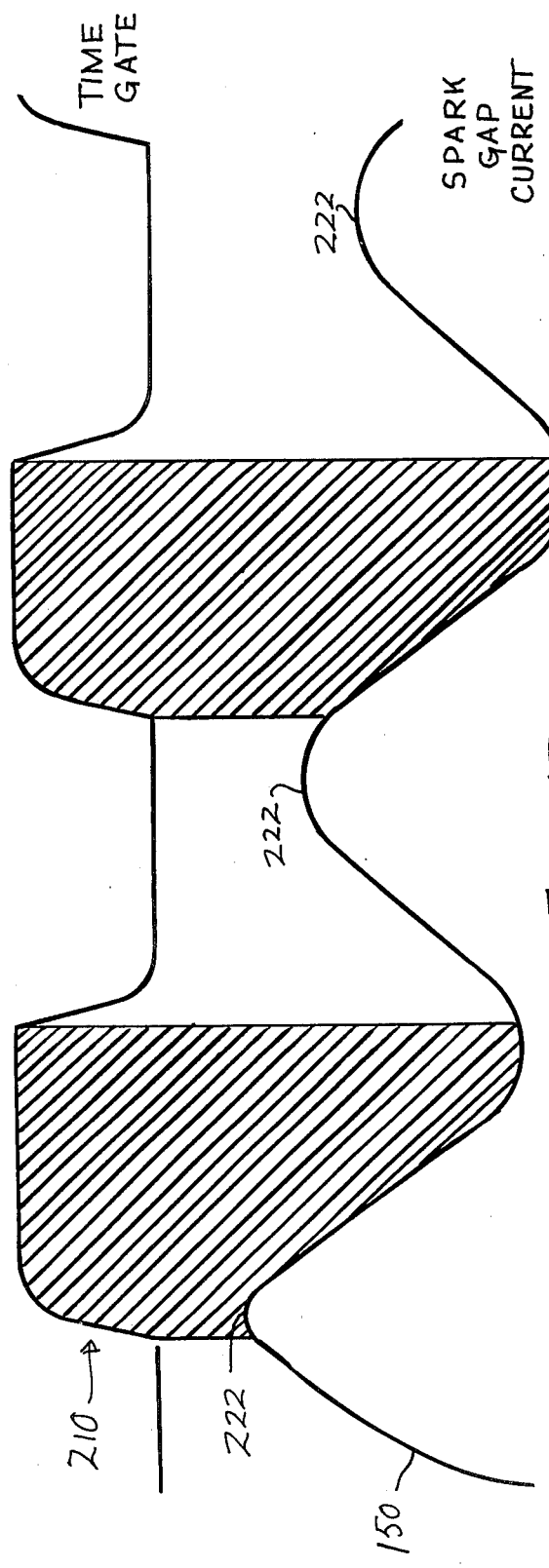
FIG. 13 comprises greatly enlarged waveform diagrams, corresponding to the initial portion of FIG. 10, and showing the relationship between the spark gap current waveform and the time gate pulses.
Figure 14:
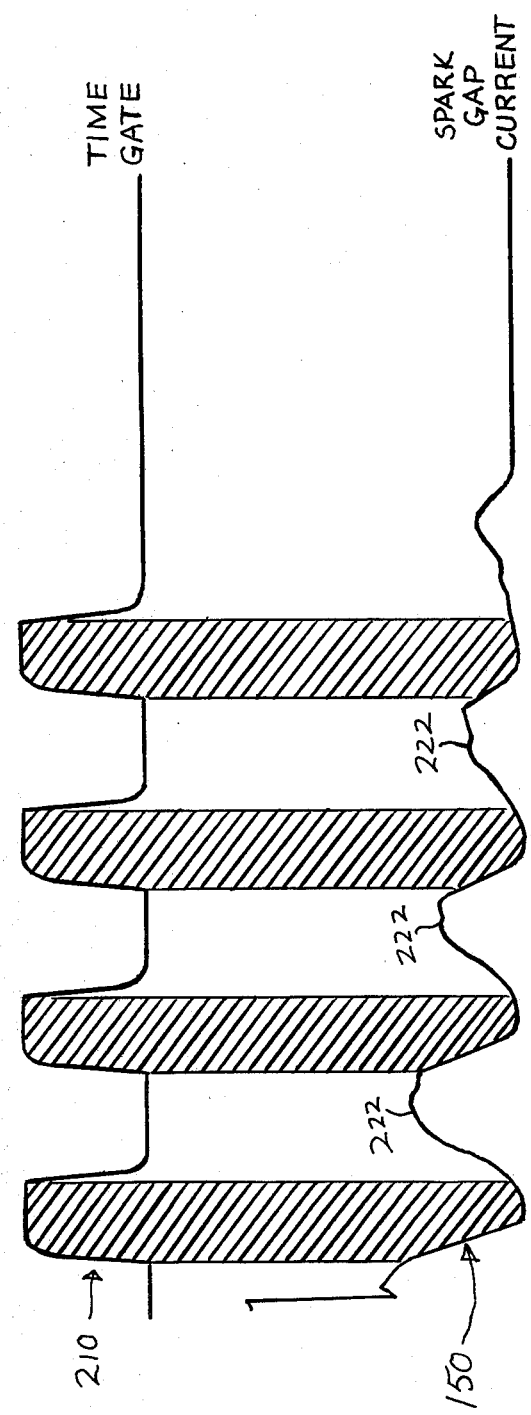
FIG. 14 comprises greatly enlarged waveform diagrams, corresponding to the final portion of FIG. 10, and showing the relationship between the spark gap current waveform and the time gate pulses.

FIG. 8 includes another sample spark gap current waveform 150, corresponding with the previously mentioned parent or capacitor current waveform 130. An enlarged version of the parent current waveform 130 is shown in FIG. 9. Greater enlargements of the initial and final portions of the parent current waveform 130 are shown in FIGS. 11 and 12. FIG. 10 shows an enlarged version of the spark gap current waveform 150. Versions having greater enlargement are shown in FIGS. 13 and 14, which show the initial and final portions of the spark gap current waveform 150.

Returning to FIG. 1A, the spark type light source 20 includes means for producing control and measurement signals corresponding with the spark gap current, the parent or capacitor current, and the diode or rectifier current. Such means may include current transformers 152, 154 and 156, mounted around leads 162, 164 and 166 which are in series with the spark gap 22, the capacitor 24 and the rectifier means 36. The current transformers 152, 154 and 156 generate signals corresponding in waveform and magnitude with the spark current, the capacitor or parent current, and the rectifier or diode current.

As shown in FIG. 1A, the outputs of the current transformers 152, 154 and 156 are connected to separate inputs of a multi-beam oscilloscope 160, for producing oscillograms representing the spark current, the parent current, and the diode current. The oscilloscope 160 may utilize a cathode ray tube having three separate electron beams, or three separate cathode ray tubes, or an oscilloscope having computerized input multiplexing or any other suitable arrangement for producing oscillograms corresponding with the spark current, the parent current and the diode current.

FIG. 1A includes a diagrammatic illustration of a system 170 adapted to utilize the light from the spark gap 22 for spectroscopic analysis. Such system 170 includes a spectrometer 172 which receives the light from the spark gap 22 and produces a spectrum of such light, by the use of a grating or the like. Any particular spectral line or band from such spectrum may be supplied to a sensitive photodetector 174, which may utilize a photomultiplier or the like to produce electrical signals corresponding to the incoming light. As shown, the output signals from the photodetector 174 are transmitted through an electronic gate 176 to an electronic integrator, which produces an output signal representing the time integral of the input signals. The integrated output of the integrator 178 is supplied to an output measuring device 180, which may be in the form of a recording electrical instrument or meter, for measuring and recording electrical currents or voltages. In this way, the intensity of any particular spectral line or band may be measured and recorded. In many cases, the measured intensity may be employed as a quantitative indication of the concentration of a particular chemical element in the material to be analyzed.

The spark type light source 20 of FIG. 1A preferably includes a time gate pulse generator 184 which is employed to select advantageous segments of the pulsating light generated by the spark gap 22, so as to improve the signal to noise ratio of the spectroscopic analytical system 170. By selecting advantageous segments of the light from the spark gap 22, it is possible to enhance the ratio between the desired signals and background signals or noise. Such desired signals may be the signals from particular spectral lines or bands. The background signals or noise may constitute a continuum which tends to mask the desired signals. Improving the signal to noise ratio enhances the sensitivity and the accuracy of the spectroscopic analytical measurements produced by the system 170.

The time gate pulse generator 184 produces time gate pulses which are supplied to the electronic gate 176 to enable the gate or turn it ON, whereby the signals corresponding to advantageous segments of the light are selected. The time gate pulses have a variable synchronized relationship with the pulsating oscillatory spark current waveform.

The time gate pulse generator 184 may include means for deriving a wave train signal corresponding with one of the currents or voltages in the charging and discharging circuit 40 for the capacitor 24, means for converting such wave train signal into pulses, and means for processing such pulses in some instances. Such processing means may include means for introducing a variable delay in such pulses, and means for varying the duration of such pulses.

FIG. 2A, which is very similar to FIG. 1A, illustrates a slightly modified spark type light source 196, which is the same as the light source 20 of FIG. 1A, except that the time gate pulse generator 184 of FIG. 1A is replaced with a slightly modified time gate pulse generator 198 which derives a wave train signal corresponding with the parent or capacitor current, rather than the diode current. Thus, the output of the current transformer 154 is connected to the input of the comparator 188, for comparison with the variable threshold signal from the component 190, to produce time gate pulses which are generally square in waveform. In some cases, such time gate pulses may be processed or modified by the variable delay circuit 192 and the variable duration circuit 194.

Thus, the time gate pulses produced in the light source 196 of FIG. 2A are related to the capacitor or parent current waveform, rather than to the diode current waveform. Otherwise, the light source 196 of FIG. 2A may be the same as the light source 20 of FIG. 1A.

FIG. 2B shows another slightly modified spark type light source 200 which is the same as the light source 20 of FIG. 1A, except that the time gate pulse generator 184 is replaced with a modified time gate pulse generator 202, adapted to derive a wavetrain signal from the spark current, rather than from the diode current. Thus, the input of the comparator 188 in the threshold detector 186 is connected to the output of the spark current transformer 152, rather than to the diode current transformer 156. Accordingly, the comparator 188 produces time gate pulses related to the spark current pulses, rather than to the diode current pulses. The time gate pulses from the comparator 188 may be modified or processed by the variable delay circuit 192 and the variable duration circuit 194, as before.

Thus, the spark type light source 200 of FIG. 2B derives the time gate pulses from the spark current, rather than from the diode current. Otherwise, the spark type light source 200 of FIG. 2B may be the same as the light source 20 of FIG. 1A.

FIG. 7A shows a sample waveform 210 of the time gate pulses and indicates the manner in which the time gate pulses may be derived from the diode current waveform 148, which is unidirectional, pulsating and oscillatory, as previously indicated. It will be seen that the diode current waveform 148 comprises a series of peaks 212 on one side of the zero axis 214. A series of valleys or minimums 216 are interspersed between the peaks 212, such minimums being approximately at the zero axis 214.

As previously indicated, the time gate pulses 210 can be derived from the diode current waveform 148 by the use of the threshold detector 186 of FIG. 1A, including the comparator 188 and the variable threshold control 190. For example, the diode current waveform 148 may be compared with a threshold level 218, established by the variable threshold control 190. When the diode current waveform 148 is below the threshold level 218, the output of the comparator 188 is zero or OFF. When the diode current waveform 148 exceeds the threshold level 218, the output of the comparator 188 is One, corresponding to ON. Thus, the time gate pulses 210 are generated with a square waveform, as indicated in FIG. 7A. The time gate pulses 210 may be delayed by the variable delay circuit 192. In FIG. 7A, the pulses 210 are shown slightly delayed.

FIG. 7A also shows a sample relationship between the time gate pulses 210 and the spark gap current waveform 146, which is unidirectional, pulsating and oscillatory, as previously indicated. Thus, the spark current waveform 146 comprises a series of peaks 222 alternating with a series of valleys or minimums 224, near the zero axis. The ON portions of the time gate pulses 210 are synchronized with off peak portions of the spark current waveform 146, including the minimum portions 224. Thus, in the light source 20 of FIG. 1A, the time gate pulses 210 select the light from such off peak portions of the spark current waveform 146, for use in spectroscopic analysis. It has been found that the selection of such off peak portions, when the spark current and the background and plasma line light intensities are relatively low, is advantageous, because the signal to noise ratio is improved. The off peak portions of the spark current produce less complex spectra than the peak portions 222, so that the background continuum in the spectrum is reduced. Thus, the measurements of the intensity of the spectral lines can be accomplished with improved sensitivity and accuracy.

By varying the delay of the time gate pulses, the selection of the off peak portions of the spark gap waveform 146 can be varied, as will be evident from FIG. 7A. The duration or length of the time gate pulses 210 can also be varied by the use of the variable duration circuit 294. By thus varying the duration of the time gate pulses 210, a further control is possible over the selection of advantageous off peak portions of the spark current waveform 146. Indeed, by varying the delay and the duration of the time gate pulses 210, any desired portions of the spark current waveform 146 can be selected for use in spectroscopic analysis.

The time gate pulses 210 can also be varied by varying the threshold level 218, as will be evident from FIG. 7A. Raising the threshold level 218 has the effect of delaying the time gate pulses 210 and shortening the duration of such pulses. Thus, raising the threshold level 218 changes the portions of the spark gap current waveform 146 which are selected by the time gate pulses 210 in the spectroscopic system 170 of FIG. 1A. Reducing the threshold level 218 has the effect of advancing and lenghtening the time gate pulses 210. Such changes can be made dynamically, under computer control, or by equivalent means.

As will be seen from FIG. 7A, the peaks 212 of the diode current waveform 148 are delayed relative to the peaks 222 of the spark gap current waveform 146. It will be seen, in fact, that the peaks 212 of the diode current are roughly synchronized with the minimums 224 of the spark gap current 146. Because of this delayed timing of the peaks 212 of the diode current 148, the time gate pulses 210 are correspondingly delayed, when such pulses are derived from the diode current waveform 148. Thus, it often is not necessary to produce any additional delay of the time gate pulses 210 by the use of the variable delay circuit 192. Accordingly, the variable delay circuit 192 may be omitted or adjusted to a delay of zero. It also may be unnecessary to change the duration of the time gate pulses 210, in which case the variable duration circuit 194 may be omitted or adjusted to cause no change in the duration of the time gate pulses.

The timing of the diode current pulses 212 is due to the operation of the charging and discharging circuit 40 for the capacitor 24, when the capacitor is discharged across the spark gap 22. Due to the cooperative action between the capacitor 24 and the three inductance coils 31, 32 and 33, the capacitor or parent current waveform 126 is in the form of a damped oscillatory wave train, oscillating between opposite sides of the zero axis 230. The waveform of the capacitor current 126 is generally sinusoidal, but is damped, so that the amplitude of the wave train decreases with time and eventually dies out entirely after a number of cycles. The capacitor current waveform 126 comprises alternate peaks 231 and 232 of opposite polarities. As shown in FIG. 7A, the peaks 231 include the first, third and fifth peaks, and all of the other odd numbered peaks. The alternate peaks 232 include the second and fourth peaks and all other even numbered peaks. Thus, the odd numbered peaks 231 are of one polarity, while the even numbered peaks 232 are of the opposite polarity. In the operation of the circuit 40 of FIG. 1a, the odd numbered peaks 231 are positive in polarity, while the even numbered peaks 232 are negative in polarity, because the capacitor 24 is initially charged to a positive voltage.

When the thyratron switching tube 48 is triggered into conductivity by a pulse supplied to its grid by the timing pulse generator 110, the full voltage across the capacitor 24 is applied across the spark gap 22. Such voltage is sufficient to ionize or break down the spark gap 22, so that the gap becomes conductive. As a result, an electrical current starts to flow from the capacitor 24 through the inductance coils 31 and 32, and also across the spark gap 22 and through the switching tube 48. Due to the inductance of the coils 31 and 32, the capacitor current 126 rises to the first peak 231 and then diminishes as the capacitor 24 is recharged with the opposite polarity. The first peak 222 of the spark gap current corresponds generally with the first peak 231 of the capacitor discharge current 126. Initially, the diode bridge 36 is nonconductive, because the diode bridge is reverse biased by the initial capacitor voltage. However, when the capacitor 24 is charged with the opposite polarity, as mentioned above, the diode bridge 36 becomes conductive between its terminals 36e and 36f. Due to the inductance of the third coil 33, the diode current rises to its first peak 212 and then diminishes as the capacitor 24 is again recharged to its original polarity. The diode bridge 36 prevents reversal of the diode current, so that the spark current 146 again rises to its second peak 222, as the capacitor 24 again discharges from its original polarity.

Thus, due to the combined action of the diode or rectifier means 36 and the inductance coils 31, 32 and 33, the peaks 222 of the spark gap current correspond generally with the positive peaks 231 of the capacitor or parent current 126, while the peaks 212 of the diode current 148 correspond with the negative peaks 232 of the capacitor current 126. By adjusting the inductance coil 32 in the spark gap path 44, the spark current will be kept unidirectional, so that the thyratron switching tube 48 will remain ionized and conductive during the entire parent current wave train 126. This is an advantageous mode of operation, because there is no reversal of the voltage across the thyratron tube 48, and no need to retrigger the tube into conductivity, except at the beginning of each spark discharge wave train 126. It is believed that this mode of operation prolongs the useful life of the thyratron switching tube 48.

FIGS. 7B and 8-14 illustrate other sample waveforms of the time gate pulses 210. FIG. 7B shows the time gate pulses 210 in relation to the parent or capacitor current wave train 128 and the spark gap current wave train 150. The time gate pulses 210 are timed to select the light from off peak portions of the spark gap current waveform 150.

In FIG. 8, the time gate pulses 210 are shown in relation to the parent or capacitor current waveform 130 and the spark gap current waveform 150. FIGS. 9-14 show enlarged versions of the time gate pulses 210 and the parent and gap current waveforms 130 and 150, to illustrate the relationships more clearly, as represented by the shaded areas.

The time gate pulses 210 of FIGS. 8-14 may be derived from the diode current waveform 148, as described in connection with FIGS. 1A and 7A. Alternatively, the time gate pulses 210 may be derived from the parent current waveform, by the modified light source 196 of FIG. 2A, in which the parent current waveform is processed by the threshold detector 186, the variable delay circuit 192 and the variable duration circuit 194. For example, the time gate pulses 210 may be derived from the positive or odd numbered peaks 231 of the parent waveform 130, following which sufficient delay may be introduced by the variable delay circuit 192 to shift the time gate pulses 210 to the relationship indicated by the shaded areas in FIGS. 9, 11 and 12.

As a further alternative, the time gate pulses 210 may be derived from the spark gap current waveform 150 by the modified light source 200 of FIG. 2B, whereby the time gate pulses 210 are derived from the peaks 222 of the spark gap current waveform 150. The pulses 210 are produced by the threshold detector 186 and are processed by the variable delay circuit 192 and the variable duration circuit 194. Sufficient delay may be introduced by the variable delay circuit 192 to shift the time gate pulses 210, as shown in FIGS. 10, 13 and 14, so that the time gate pulses 210 correspond with the desired off peak portions of the spark gap current waveform 150, as indicated by the shaded areas in FIGS. 10, 13 and 14.

It is advantageous to provide low damping in the discharging portion of the circuit 40 for the capacitor 24, so that the damped oscillatory wave train of the capacitor discharge current will have a large number of cycles, as indicated by the parent current oscillogram 130 of FIGS. 8–14. In this way, the spark gap current waveform 150 also has a large number of cycles. The off peak portions of all of the cycles are available to produce light for spectroscopic analysis and for selection by the time gate pulses 210. The utilization of all three inductance coils 31, 32 and 33 is conducive to low damping in the capacitor discharge circuit, as are very high quality low loss capacitors, such as those of glass-mica construction.

The cooperative circuit arrangement involving the capacitor 24, the spark gap 22, the diode bridge rectifier 36, and the three inductance coils 31, 32 and 33 in series with the capacitor, the spark gap and the diode rectifier bridge, results in a parent or capacitor current in the form of a damped oscillatory wave train, having a low damping factor, and thus containing a large number of oscillatory cycles. The diode current and preferably also the spark gap current have pulsating oscillatory unidirectional waveforms with a large number of cycles. This cooperative circuit arrangement is distinctly different from and represents a significant improvement over the construction disclosed in the previously mentioned U.S. patent application of John A. Bernier, entitled "High-Voltage Spark Source". In the Bernier construction, there is only one inductance coil, which is connected in series with the spark gap. The Bernier construction employs a high voltage alternating current transformer and a bridge rectifier to charge the capacitor. The direct current output terminals of the bridge rectifier are connected directly across the capacitor, without any inductance coil in series with the bridge rectifier or the capacitor. With this construction, the bridge rectifier prevents any great recharging of the capacitor with a reversed polarity, after the initial discharge of the capacitor through the spark gap. Thus, there is only a small oscillation of the capacitor current and voltage, and such oscillation is soon damped out, after a few cycles. The spark gap current is prolonged and kept unidirectional by the inductance coil in the Bernier construction, so that the spark gap current has only a few small oscillations, without changing polarity. The prolonged spark gap current flows through the bridge rectifier, after the initial discharge of the capacitor. Thus, the Bernier construction produces a spark gap current with only a single prolonged unidirectional pulse, with only a few small oscillations which are too small to change the polarity of the pulse.

In the charging and discharging circuit 40 of the present application, as shown in FIGS. 1A and 1B, the capacitor 24 is charged by the voltage from the high voltage secondary winding 60b, through the current limiting impedance 62 and the diode rectifier bridge 36. When the capacitor 24 is discharged across the spark gap 22, the diode bridge rectifier 36 cooperates with the three inductance coils 31, 32 and 33 to cause the parent or capacitor current to be oscillatory with a low damping, while causing the diode current to have a pulsating oscillatory unidirectional waveform. The spark gap current is also caused to have a pulsating oscillatory unidirectional waveform, or at least to have a unidirectional component, depending upon the adjustment of the three inductance coils 31, 32 and 33. During the capacitor discharging portion of the oscillating cycle, the diode bridge rectifier 36 is conductive between its terminals 36e and 36f. The diodes 36a and 36b are in parallel with the diodes 36c and 36d. During the capacitor discharging portion of the operating cycle, the impedance 62 has an isolating effect between the high voltage secondary winding 60b and the diode bridge rectifier 36. When the discharge of the capacitor 24 through the spark gap 22 has been completed, the capacitor 24 is again charged from the high voltage secondary winding 60b through the diode bridge rectifier 36.

The present invention improves the precision (repeatability) of the detected light signals by separating the time at which the signal from the sample electrode is detected from the time at which the light source emits a signal from both the sample electrode and the current carrying spark plasma (or "channel"). The latter case contains two sources of imprecision, while the former only one, implying higher and more meaningful precision in the former.

Because most emission spectrochemical methods use calibration standards to prepare graphs or graphical relations between emitted light intensity and elemental concentration, it follows that improvements in the precision of individual determinations of light intensity will provide better definition of the functional relationship between the light intensity and elemental composition of the sample electrode being analyzed. Thus, it follows that improvements in precision (as above) will give corresponding improvements in accuracy for those parts of the analysis tracable to the concentration-intensity relation.

In utilizing the time gate pulses 210 to select segments of the spark-generated light for spectroscopic analysis, it has been found that it is advantageous to select the light which is produced when the spark gap current is decreasing, while rejecting the light which is produced when the spark gap current is increasing or is at its peak values. When the spark gap current is decreasing, the undesirable background radiation or noise is significantly decreased, while the intensity of the spectral lines due to the sample material remains high, so that the signal to noise ratio is greatly improved.

This favorable relationship between the time gate pulses 210 and the spark gap current waveform 150 is shown in the oscillograms of FIG. 10 and also in the enlarged oscillograms of FIGS. 13 and 14. The shaded areas represent the segments of the spark gap current waveform 150 which are selected by the time gate pulses 210. As to such shaded areas, it will be seen that the spark gap current is decreasing, and that the slope of the selected segments of the waveform 150 is negative. Thus, the derivative of the spark gap current with respect to time is negative. Such derivative may be represented as $di/dt$.

When the spark gap current is decreasing, the spark discharge is in a state of relaxation. The undesirable background radiation or noise from the spark channel or plasma is reduced, while the light from the sample electrode remains at a high intensity, so that the signal to noise ratio is high.

We claim:

1. An electric spark type light source for producing light for spectroscopic analysis, comprising
   an analytical spark gap, an energy storage capacitor,
a charging and discharging circuit for alternately charging said capacitor and causing said capacitor to discharge across said spark gap to produce sparks which generate light for spectroscopic analysis,
said circuit including at least one inductance coil for causing the discharge current through said spark gap to be oscillatory and pulsating in waveform,
said circuit including rectifier means for causing the discharge current through said spark gap to have at least a unidirectional component,
and time gate pulse generating means for deriving time gate pulses from said circuit with said time gate pulses synchronized with the oscillatory pulsating waveform of the spark gap current for use in selecting repetitive segments of the light from said sparks for use in spectroscopic analysis.

2. An electric spark type light source according to claim 1,
said time gate pulse generating means comprising means for deriving a rectifier signal corresponding to the current through said rectifier means,
and means for converting said rectifier signal into a train of time gate pulses.

3. An electric spark type light source according to claim 1,
said time gate pulse generating means including means for deriving a rectifier signal corresponding to the current through said rectifier means,
and a threshold detector for converting said rectifier signal into a train of time gate pulses.

4. An electric spark type light source according to claim 1,
said time gate pulse generating means comprising means for deriving a capacitor discharge signal corresponding to the discharge current from said capacitor,
and means for converting said capacitor discharge signal into a train of time gate pulses.

5. An electric spark type light source according to claim 1,
said time gate pulse generating means comprising means for deriving a capcitor discharge signal corresponding to the discharge current from said capacitor,
and a threshold detector for converting said capacitor discharge signal into a train of time gate pulses.

6. An electric spark type light source according to claim 5,
including variable delay means for producing a variable delay in said train of time gate pulses.

7. An electric spark type light source according to claim 1,
said time gate pulse generating means comprising means for deriving a spark current signal corresponding to the discharge current across said spark gap,
and means for converting said spark current signal into a train of time gate pulses.

8. An electric spark type light source according to claim 1,
said time gate pulse generating means including means for deriving a spark current signal corresponding to the discharge current across said spark gate,
and a threshold detector for converting said spark current signal into a train of time gate pulses.

9. An electric spark type light source according to claim 8,
including variable delay means for producing a variable delay in said train of time gate pulses.

10. An electric spark type light source according to claim 1,
said time gate pulse generating means including means for deriving a wave train signal corresponding to one of the oscillatory pulsating currents in said circuit due to the discharge of said capacitor across said spark gap,
and means for converting said wave train signal into a train of time gate pulses.

11. An electric spark type light source according to claim 10,
including variable delay means for producing a variable delay in said train of time gate pulses.

12. An electric spark type light source according to claim 10,
including pulse processing means for modifying said train of time gate pulses.

13. An electric spark type light source according to claim 10, including
variable duration means for modifying the duration of said time gate pulses.

14. An electric spark type light source according to claim 1,
including means for deriving a wave train signal corresponding to one of the oscillatory currents in said circuit due to the discharge of said capacitor across said spark gap,
and a threshold detector for converting said wave train signal into a train of time gate pulses.

15. An electric spark type light source according to claim 14,
including pulse processing means for modifying said time gate pulses.

16. An electric spark type light source according to claim 14,
including variable delay means for producing a variable delay in said time gate pulses.

17. An electric spark type light source according to claim 1,
in which said circuit comprises a spark gap path including said analytical spark gap,
a capacitor path including said capacitor,
and a rectifier path including said rectifier means,
said spark gap path being connected across said capacitor path for receiving the discharge current from said capacitor,
said rectifier path being connnected in parallel with said spark gap path,
said time gate pulse generating means including means for deriving a wave train signal corresponding to the current in one of said paths,
and means for converting said wave train signal into a train of time gate pulses.

18. An electric spark type light source according to claim 17,
in which said circuit comprises a first inductance coil in series with said capacitor path,
a second inductance coil in series with said spark gap path,
and a third inductance coil in series with said rectifier path.

19. An electric spark type light source according to claim 18, including electronic switching means in series with said spark gap path for initiating the discharge of said capacitor across said spark gap.

20. An electric spark type light source according to claim 18, in which at least one of said inductance coils includes means for changing the inductance thereof.

21. An electric spark type light source according to claim 17, including electronic switching means in series with said spark gap path for initiating the discharge of said capacitor across said spark gap.

22. An electric spark type light source according to claim 17, including
variable delay means for producing a variable delay in said time gate pulses,
and variable duration means for modifying the duration of said time gate pulses by a variable amount.

23. An electric spark type light source according to claim 1,
in which said circuit comprises a capacitor path including said capacitor and a first inductance coil in series with said capacitor;
a spark gap path including said spark gap and a second inductance coil in series with said spark gap,
and electronic switching means in series with said spark gap for initiating the discharge of said capacitor across said spark gap;
and a rectifier path including said rectifier means and a third inductance coil in series with said rectifier means;
said spark gap path being connected across said capacitor path for receiving the discharge current from said capacitor;
said rectifier path being connected in parallel with said spark gap path;
said time gate pulse generating means including means for deriving a wave train signal corresponding to the current in one of said paths,
and means for converting said wave train signal into a train of time gate pulses.

24. An electric spark type light source according to claim 23,
in which said circuit comprises a charging path including power supply means for charging said capacitor.

25. An electric spark type light source according to claim 23,
said rectifier means comprising a bridge rectifier having output terminals connected into said rectifier path,
said bridge rectifier having input terminals,
said circuit including a charging path connected across said input terminals and including an alternating current power supply for charging said capacitor.

26. An electric spark type light source according to claim 25,
in which said alternating current power supply comprises an alternating current power transformer having a high voltage secondary winding connected into said charging path,
and impedance means connected in series with said high voltage secondary winding for limiting the charging current delivered by said winding.

27. An electric spark type light source according to claim 1,
said time gate pulse generating means being constructed and arranged to synchronize said time gate pulses with segments of the oscillatory pulsating waveform of the spark gap current when the spark gap current is decreasing.

28. An electric spark type light source for producing light for spectroscopic analysis comprising
an analytical spark gap,
an energy storage capacitor,
and a charging and discharging circuit for alternately charging said capacitor and causing said capacitor to discharge across said spark gap to generate sparks which produce light for spectroscopic analysis,
said circuit including rectifier means for causing the discharge current through said spark gap to have at least a unidirectional component,
said rectifier means comprising a bridge rectifier having a pair of direct current output terminals and a pair of alternating current input terminals,
said circuit comprising a capacitor path including said capacitor,
a spark gap path including said spark gap,
and a rectifier path including said direct current output terminals of said bridge rectifier,
said circuit comprising a first inductance coil in series with said capacitor path,
a second inductance coil in series with said spark gap path,
and a third inductance coil in series with said rectifier path,
said spark gap path being connected across said capacitor path for receiving the discharge current form said capacitor,
said rectifier path being connected in parallel with said spark gap path,
said inductance coils and said rectifier means producing an oscillatory discharge current in said capacitor path,
an oscillatory pulsating unidirectional discharge current in said rectifier path,
and an oscillatory pulsating discharge current with at least a unidirectional component in said spark gap path,
said circuit comprising an alternating current power supply connected across said alternating input terminals of said bridge rectifier for charging said capacitor.

29. An electric spark type light source according to claim 28,
in which said alternating current power supply comprises an alternating current power transformer having a high voltage secondary winding connected across said alternating current input terminals of said bridge rectifier,
and impedance means connected in series with said secondary winding for limiting the charging current delivered by said secondary winding.

30. An electric spark type light source according to claim 28,
including switching means connected in series with said spark gap path for initiating the discharge of said capacitor across said spark gap.

31. An electric spark type light source according to claim 28,
including electronic switching means connected in series with said spark gap path for initiating the discharge of said capacitor across said spark gap.

32. An electric spark type light source according to claim 28, including a thyratron electronic switching tube connected in series with said spark gap path for initiating the discharge of said capacitor across said spark gap.

33. A method of performing a spectroscopic analysis, comprising the steps of producing electric sparks by utilizing a spark current having an oscillatory pulsating waveform, causing said sparks to act upon a sample material to be analyzed and thereby producing light for spectroscopic analysis, and utilizing repetitive segments of said light during repetitive time intervals when said oscillatory pulsating waveform of the spark current is decreasing in magnitude, whereby a high signal to noise ratio is realized.

* * * * *